US012311182B2

United States Patent
Greenhut et al.

(10) Patent No.: US 12,311,182 B2
(45) Date of Patent: May 27, 2025

(54) DEVICE AND METHOD FOR ATRIAL TACHYARRHYTHMIA DETECTION

(71) Applicant: Medtronic, Inc., Minneapolis, MN (US)

(72) Inventors: Saul E. Greenhut, Denver, CO (US); Mark L. Brown, North Oaks, MN (US); Vincent P. Ganion, Blaine, MN (US); Yanina Grinberg, Plymouth, MN (US); Troy E. Jackson, Rogers, MN (US); Todd J. Sheldon, North Oaks, MN (US); Shravya Srigiri, Minneapolis, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 406 days.

(21) Appl. No.: 17/669,294

(22) Filed: Feb. 10, 2022

(65) Prior Publication Data

US 2022/0288387 A1    Sep. 15, 2022

Related U.S. Application Data

(60) Provisional application No. 63/160,541, filed on Mar. 12, 2021.

(51) Int. Cl.
*A61N 1/36*  (2006.01)
*A61N 1/362*  (2006.01)
*A61N 1/365*  (2006.01)

(52) U.S. Cl.
CPC ........... *A61N 1/365* (2013.01); *A61N 1/3624* (2013.01)

(58) Field of Classification Search
CPC .. A61N 1/365; A61N 1/3624; A61N 1/36578; A61N 1/3756; A61N 1/0563; A61N 1/36507; A61N 1/3684; A61N 1/39622; A61B 5/353; A61B 5/361; A61B 5/363; A61B 5/4836; A61B 5/686; A61B 5/6869; A61B 5/318; A61B 5/352
See application file for complete search history.

(56) References Cited

U.S. PATENT DOCUMENTS

| 5,507,782 A | 4/1996 | Kieval et al. |
| 5,683,426 A | 11/1997 | Greenhut et al. |
| 5,713,932 A * | 2/1998 | Gillberg ............... A61N 1/3622 607/9 |
| 6,810,283 B2 | 10/2004 | Suribhotla et al. |

(Continued)

OTHER PUBLICATIONS

Brown et al., "Sensing and detection in Medtronic implantable cardioverter defibrillators," Herzschrittmacher.Apie I'nd Eijektrophysiologie/ Steinkopff, Darmstadt, DE, vol. 27, No. 3, Sep. 8, 2016, pp. 193-212.

(Continued)

*Primary Examiner* — Rex R Holmes

(57) ABSTRACT

A medical device is configured to sense a cardiac electrical signal and detect an atrial tachyarrhythmia based on the sensed cardiac electrical signal. The medical device is configured to determine that far field oversensing criteria are met by the cardiac electrical signal during the detected atrial tachyarrhythmia. The medical device may detect termination of the detected atrial tachyarrhythmia in response to the far field oversensing criteria being met.

19 Claims, 14 Drawing Sheets

(56) References Cited

U.S. PATENT DOCUMENTS

| | | | |
|---|---|---|---|
| 7,398,123 B1 | 7/2008 | Levine | |
| 7,818,056 B2 | 10/2010 | Kim et al. | |
| 8,050,750 B2 | 11/2011 | Jackson | |
| 8,086,307 B2* | 12/2011 | Virag | A61N 1/368 607/5 |
| 8,332,033 B2 | 12/2012 | Reed et al. | |
| 9,889,303 B2 | 2/2018 | Brown et al. | |
| 10,463,269 B2 | 11/2019 | Boleyn et al. | |
| 2016/0015985 A1 | 1/2016 | Cho et al. | |
| 2016/0113577 A1 | 4/2016 | Cao et al. | |
| 2017/0281034 A1 | 10/2017 | Higgins et al. | |
| 2018/0069199 A1 | 3/2018 | Bonner et al. | |
| 2019/0083800 A1 | 3/2019 | Yang et al. | |
| 2019/0192020 A1* | 6/2019 | Cao | A61B 5/316 |

OTHER PUBLICATIONS

European Search Report Completed Jul. 25, 2022, European Patent Application No. 22159919.4, 8 pages.
Koivisto et al., "Automatic Detection of Atrial Fibrillation using MEMS accelerometer", Computing in Cardiology 2015, Sep. 6, 2015, pp. 829-832.
European Office Action dated Oct. 31, 2024, corresponding to European Patent Application No. 22159919.4, 5 pages.

* cited by examiner

DEVICE AND METHOD FOR ATRIAL TACHYARRHYTHMIA DETECTION

REFERENCE TO RELATED APPLICATION

This application claims the benefit of provisional U.S. Patent Application No. 63/160,541, filed Mar. 12, 2021, incorporated herein by reference in its entirety.

TECHNICAL FIELD

This disclosure relates to a medical device and method for detecting atrial tachyarrhythmia.

BACKGROUND

During normal sinus rhythm (NSR), the heartbeat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles, sometimes referred to as the "His-Purkinje system."

Patients with a conduction system abnormality, e.g., SA node dysfunction or poor AV node conduction, bundle branch block, or other conduction abnormalities, may receive a pacemaker to restore a more normal heart rhythm. A single chamber pacemaker coupled to a transvenous lead carrying electrodes positioned in the right atrium may provide atrial pacing to treat a patient having SA node dysfunction. Intracardiac pacemakers have been introduced or proposed for implantation entirely within a patient's heart eliminating the need for transvenous leads. For example, an atrial intracardiac pacemaker may provide sensing and pacing from within an atrial chamber of a patient having bradycardia or SA node dysfunction. When the AV node is functioning normally, single chamber atrial pacing may sufficiently correct the heart rhythm. The pacing-evoked atrial depolarizations may be conducted normally to the ventricles via the AV node and the His-Purkinje system for maintaining normal AV synchrony.

Atrial tachyarrhythmias are atrial rhythms that may arise from a non-sinus node location and can occur with a relatively high rate of incidence, even in a patient having an atrial pacemaker. Atrial fibrillation may be the most common form of arrhythmia. Non-sinus atrial tachycardia (AT) and atrial fibrillation (AF) can lead to serious and life-threatening complications, including blood clots, stroke, heart failure and more serious arrhythmias. Atrial tachyarrhythmias, while highly prevalent, tend to be underdiagnosed and undertreated.

SUMMARY

The techniques of this disclosure generally relate to a medical device configured to sense a cardiac electrical signal and analyze the cardiac electrical signal for detecting an atrial tachyarrhythmia and/or atrial fibrillation (AT/AF) episode and detecting termination of the AT/AF episode. The techniques disclosed herein may be used to detect AT/AF and the termination of AT/AF in the presence of oversensing of far field R-waves (FFRWs) from the cardiac electrical signal sensed from an atrial location. The medical device may be configured to switch from a non-AT/AF operating state to an AT/AF onset operating state in response to determining that AT/AF onset criteria are met by the cardiac electrical signal. When termination criteria are not met by the cardiac electrical signal prior to a detection time interval expiring during the AT/AF onset operating state, the medical device may switch to an AT/AF detection state and track the time duration of the detected AT/AF episode.

The medical device may switch to a pending termination state when termination criteria are met by the cardiac electrical signal during the AT/AF detection state. According to some examples, if the AT/AF onset criteria are determined to be met by the cardiac electrical signal prior to a termination timer expiring during the pending termination state, the medical device may return to the AT/AF detection state and continue tracking the duration of the detected AT/AF episode. In response to the AT/AF onset criteria not being met prior to expiration of the termination timer in the pending termination state, the medical device may detect termination of the detected AT/AF episode and return to the non-AT/AF operating state. In various examples, determining that AT/AF onset criteria are met may include determining that less than a threshold number of sequences of multiple atrial event cycles are classified as FFRW oversensing sequences. Determining that termination criteria are met may include, among other things, determining that greater than a threshold number of sequences of multiple atrial event cycles are classified as FFRW oversensing cycles.

In one example, the disclosure provides a medical device including a sensing circuit configured to sense a cardiac electrical signal and a control circuit configured to detect an atrial tachyarrhythmia based on the sensed cardiac electrical signal. The control circuit is configured to determine that far field oversensing criteria are met by the cardiac electrical signal during the detected atrial tachyarrhythmia and may detect termination of the detected atrial tachyarrhythmia in response to at least the far field oversensing criteria being met. In some examples, the control circuit may start a termination time interval in response to determining that the far field oversensing criteria are met. During the termination time interval, the control circuit may determine if atrial tachyarrhythmia onset criteria are met based on at least the cardiac electrical signal. The control circuit may continue detecting the atrial tachyarrhythmia in response to determining that the atrial tachyarrhythmia onset criteria are met prior to the termination time interval expiring. The control circuit may detect termination of the atrial tachyarrhythmia in response to the termination time interval expiring and the atrial tachyarrhythmia onset criteria not being met.

In another example, the disclosure provides a method including sensing a cardiac electrical signal and detecting an atrial tachyarrhythmia based on the sensed cardiac electrical signal. The method further includes determining that far field oversensing criteria are met by the cardiac electrical signal during the detected atrial tachyarrhythmia and detecting termination of the atrial tachyarrhythmia in response to at least the far field oversensing criteria being met. The method may include starting a termination time interval in response to determining that the far field oversensing criteria are met and determining if atrial tachyarrhythmia onset criteria are met based on at least the cardiac electrical signal during the termination time interval. The method may include continuing detecting the atrial tachyarrhythmia in response to determining that the atrial tachyarrhythmia onset criteria are met prior to the termination time interval expiring. The method may include detecting termination of the atrial tachyarrhythmia in response to the termination time interval expiring and the atrial tachyarrhythmia onset criteria not being met.

In another example, the disclosure provides a non-transitory, computer-readable storage medium storing a set of instructions which, when executed by a control circuit of a medical device, cause the medical device to sense a cardiac electrical signal and detect an atrial tachyarrhythmia based on the sensed cardiac electrical signal. The instructions may further cause the device to determine that far field oversensing criteria are met by the cardiac electrical signal during the detected atrial tachyarrhythmia. The instructions may cause the device to start a termination time interval in response to determining that the far field oversensing criteria are met. The instructions may further cause the device to determine whether atrial tachyarrhythmia onset criteria are met based on at least the cardiac electrical signal prior to the termination time interval expiring. In response to the atrial tachyarrhythmia onset criteria being met prior to the termination time interval expiring, the instructions may cause the medical device to continue detecting the atrial tachyarrhythmia. In response to the termination time interval expiring and the atrial tachyarrhythmia onset criteria not being met, the instruction may cause the medical device to detect termination of the atrial tachyarrhythmia.

Further disclosed herein is the subject matter of the following clauses:

1. A medical device comprising a sensing circuit configured to sense a cardiac electrical signal and a control circuit configured to: detect an atrial tachyarrhythmia based on the sensed cardiac electrical signal; determine that far field oversensing criteria are met by the cardiac electrical signal during the detected atrial tachyarrhythmia; and detect termination of the atrial tachyarrhythmia in response to at least the far field oversensing criteria being met.

2. The medical device of clause 1, wherein the control circuit is further configured to: detect the termination of the atrial tachyarrhythmia by: starting a termination time interval in response to determining that the far field oversensing criteria are met; during the termination time interval, determining if atrial tachyarrhythmia onset criteria are met based on at least the cardiac electrical signal; detecting the termination of the atrial tachyarrhythmia in response to the termination time interval expiring and the atrial tachyarrhythmia onset criteria not being met; and continue detecting the atrial tachyarrhythmia without detecting termination of the atrial tachyarrhythmia in response to determining that the atrial tachyarrhythmia onset criteria are met prior to the termination time interval expiring.

3. The medical device of any of clauses 1-2, wherein the control circuit is configured to determine that the far field oversensing criteria are met by: identifying a plurality of sequences of atrial cycles, each of the plurality of sequences comprising at least two consecutive atrial cycles; classifying each of the plurality of sequences of atrial cycles as one of a far-field R-wave sequence or a non-far field R-wave sequence; determining that a threshold number of the plurality of sequences are classified as far-field R-wave sequences; and determining that the far field oversensing criteria are met when at least the threshold number of the plurality of sequences are classified as far-field R-wave sequences.

4. The medical device of clause 3, wherein the sensing circuit is configured to: set a P-wave sensing threshold; and generate an atrial sensed event signal in response to the cardiac electrical signal crossing the P-wave sensing threshold; and the control circuit is further configured to classify a sequence of the plurality of sequences as a far field R-wave sequence in response to: determining that at least one peak amplitude of the cardiac electrical signal corresponding to at least three consecutive atrial sensed event signals is less than a far field R-wave peak amplitude limit, and at least one of: determining a pattern of alternating peak amplitudes of the cardiac electrical signal corresponding to at the least three consecutive atrial sensed event signals, or determining an atrial event interval between a consecutive pair of the at least three consecutive atrial sensed event signals that is greater than a predetermined long interval threshold.

5. The medical device of any of clauses 2-4, further comprising a pulse generator configured to generate atrial pacing pulses; wherein the control circuit is configured to: determine that a threshold number of atrial pacing pulses are generated during the detected atrial tachyarrhythmia; and start the termination time interval in response to the threshold number of atrial pacing pulses being generated during the detected atrial tachyarrhythmia.

6. The medical device of any of clauses 2-5, wherein: the sensing circuit is configured to: set a P-wave sensing threshold; and generate an atrial sensed event signal in response to the cardiac electrical signal crossing the P-wave sensing threshold; and the control circuit is configured to: determine atrial event intervals between consecutive atrial events comprising the atrial sensed event signals generated by the sensing circuit; during the detected atrial tachyarrhythmia, determine that a threshold number of the atrial event intervals are longer than a predetermined termination interval threshold; and start the termination time interval in response to the threshold number of the atrial event intervals being longer than the predetermined termination interval threshold.

7. The medical device of clause 6, further comprising a pulse generator configured to generate atrial pacing pulses; wherein the control circuit is configured to count an atrial event interval ending with an atrial pacing pulse generated by the pulse generator as an atrial event interval that is longer than the predetermined termination interval threshold.

8. The medical device of any of clauses of 2-7, wherein the sensing circuit is configured to: set a P-wave sensing threshold; and generate an atrial sensed event signal in response to the cardiac electrical signal crossing the P-wave sensing threshold; and the control circuit is further configured to: during the detected atrial tachyarrhythmia, determine a plurality of atrial event intervals comprising atrial sensed event signals generated by the sensing circuit; determine a count of the plurality of atrial event intervals that are longer than an atrial tachyarrhythmia detection interval; start the termination time interval in response to one of: determining that the count is greater than or equal to a first threshold, or determining that the count is less than the first threshold and greater than or equal to a second threshold and that the far field oversensing criteria are met.

9. The medical device of any of clauses 1-7, wherein the control circuit is configured to detect the atrial tachyarrhythmia by: determining that the atrial tachyarrhythmia onset criteria are met by the cardiac electrical signal; starting a detection time interval; determining that termination criteria are unmet by the cardiac electrical signal prior to expiration of the detection time interval; and detecting the atrial tachyarrhythmia in response to the detection time interval expiring with the termination criteria being unmet.

10. The medical device of clause 8, further comprising a memory and an accelerometer configured to sense an acceleration signal, wherein the control circuit is further configured to: determine an atrial rate over at least a portion of the detection time interval; and store a segment of at least one of the cardiac electrical signal and the acceleration signal in the memory in response to detecting the atrial tachyarrhythmia and the atrial rate being faster than a previously determined atrial rate of a previously detected atrial tachyarrhythmia.

11. The medical device of any of clauses 1-10, wherein the control circuit is configured to detect the atrial tachyarrhythmia by: determining that atrial tachyarrhythmia onset criteria are met by the cardiac electrical signal; starting a detection time interval; determining that termination criteria are met by the cardiac electrical signal prior to expiration of the detection time interval; starting a pending onset termination time interval with the detection time interval still running; determining that the atrial tachyarrhythmia onset criteria are met prior to the pending onset termination time interval expiring; and detecting the atrial tachyarrhythmia in response to expiration of the detection time interval.

12. The medical device of any of clauses 1-11, wherein: the sensing circuit comprises: a P-wave sensing channel configured to: set a P-wave sensing threshold; sense atrial events in response to the cardiac electrical signal crossing a P-wave sensing threshold; and a far-field R-wave sensing channel configured to: set a far-field R-wave sensing threshold; set a far-field R-wave sensing window; and sense far-field R-waves in response to the cardiac electrical signal crossing the far-field R-wave sensing threshold during the far-field R-wave sensing window; and the control circuit is configured to determine that the far field oversensing criteria are met based on at least atrial events sensed by the P-wave sensing channel and far-field R-waves sensed by the far-field R-wave sensing channel.

13. The medical device of any of clauses 1-12 further comprising a pulse generator configured to generate pacing pulses according to a pacing therapy in response to the control circuit detecting the atrial tachyarrhythmia.

14. The medical device of any of clauses 1-13 further comprising a telemetry circuitry configured to transmit an atrial tachyarrhythmia detection notification in response to the control circuit detecting the atrial tachyarrhythmia.

15. The medical device of any of clauses 1-14 further comprising:
a housing enclosing the sensing circuit and the control circuit, the housing comprising a pair of housing-based electrodes coupled to the sensing circuit for sensing the cardiac electrical signal.

16. A method comprising: sensing a cardiac electrical signal; detecting an atrial tachyarrhythmia based on the sensed cardiac electrical signal; determining that far field oversensing criteria are met by the cardiac electrical signal during the detected atrial tachyarrhythmia; and detecting termination of the atrial tachyarrhythmia in response to at least the far field oversensing criteria being met.

17. The method of clause 16, further comprising detecting the termination of the atrial tachyarrhythmia by: starting a termination time interval in response to determining that the far field oversensing criteria are met; during the termination time interval, determine if atrial tachyarrhythmia onset criteria are met based on at least the cardiac electrical signal; continuing detecting the atrial tachyarrhythmia without detecting termination of the atrial tachyarrhythmia in response to determining that the atrial tachyarrhythmia onset criteria are met prior to the termination time interval expiring; and in response to the atrial tachyarrhythmia onset criteria not being met, detecting the termination of the atrial tachyarrhythmia in response to the termination time interval expiring and the atrial tachyarrhythmia onset criteria not being met.

18. The method of any of clauses 16-17, wherein determining that the far field oversensing criteria are met comprises: identifying a plurality of sequences of atrial cycles, each of the plurality of sequences comprising at least two consecutive atrial cycles; classifying each of the plurality of sequences as one of a far-field R-wave sequence or a non-far field R-wave sequence; determining that a threshold number of the plurality of sequences are classified as far-field R-wave sequences; and determining that the far field oversensing criteria are met when at least the threshold number of the plurality of sequences are classified as far-field R-wave sequences.

19. The method of clause 18, further comprising: setting a P-wave sensing threshold; generating an atrial sensed event signal in response to the cardiac electrical signal crossing the P-wave sensing threshold; and classifying a sequence of the plurality of sequences as a far field R-wave sequence in response to: determining that at least one maximum peak amplitude of the cardiac electrical signal corresponding to at least three consecutive atrial sensed event signals is less than a far field R-wave peak amplitude limit, and at least one of: determining a pattern of alternating peak amplitudes of the cardiac electrical signal corresponding to the at least three consecutive atrial sensed event signals generated by the sensing circuit, or determining an atrial event interval between a consecutive pair of the at least three consecutive atrial sensed event signals that is greater than a predetermined long interval threshold.

20. The method of any of clauses 17-19, comprising: generating atrial pacing pulses; determining that a threshold number of atrial pacing pulses are generated during the detected atrial tachyarrhythmia; and starting the termination time interval in response to the threshold number of atrial pacing pulses being generated during the detected atrial tachyarrhythmia.

21. The method of any of clauses 17-20, comprising: setting a P-wave sensing threshold; generating an atrial sensed event signal in response to the cardiac electrical signal crossing the P-wave sensing threshold; determining atrial event intervals between consecutive atrial events comprising the atrial sensed event signals generated by the sensing circuit; during the detected atrial tachyarrhythmia, determining that a threshold number of the atrial event intervals are longer than a predetermined termination interval threshold; and starting the termination time interval in response to the threshold number of the atrial event intervals being longer than the predetermined termination interval threshold.

22. The method of clause 21, comprising: generating atrial pacing pulses; counting an atrial event interval ending with an atrial pacing pulse as an atrial event interval that is longer than the predetermined termination interval threshold.

23. The method of any of clauses 17-22, further comprising: setting a P-wave sensing threshold; generating an atrial sensed event signal in response to the cardiac electrical signal crossing the P-wave sensing threshold; during the detected atrial tachyarrhythmia, determining a plurality of atrial event intervals comprising atrial sensed event signals; determining a count of the plurality of atrial event intervals that are longer than a predetermined termination interval threshold; starting the termination time interval in response to one of: determining that the count is greater than or equal to a first threshold, or determining that the count is less than the first threshold and greater than or equal to a second threshold and that the far field oversensing criteria are met.

24. The method of any of clauses 16-23, wherein detecting the atrial tachyarrhythmia comprises: determining that the atrial tachyarrhythmia onset criteria are met by the cardiac electrical signal; starting a detection time interval; determining that termination criteria are unmet by the cardiac electrical signal prior to expiration of the detection time interval; and detecting the atrial tachyarrhythmia in response to the detection time interval expiring with the termination criteria being unmet.

25. The method of clause 24, further comprising: determining an atrial rate over at least a portion of the detection time interval; and storing a segment of at least one of the cardiac electrical signal and an acceleration signal in response to the atrial rate being faster than a previously determined atrial rate of a previously detected atrial tachyarrhythmia.

26. The method of any of clauses 16-25, wherein detecting the atrial tachyarrhythmia comprises: determining that the atrial tachyarrhythmia onset criteria are met by the cardiac electrical signal; starting a detection time interval; determining that termination criteria are met by the cardiac electrical signal prior to expiration of the detection time interval; starting a pending onset termination time interval with the detection time interval still running; determining that the atrial tachyarrhythmia onset criteria are met prior to the pending onset termination time interval expiring; and detecting the atrial tachyarrhythmia in response to expiration of the detection time interval.

27. The method of any of clauses 16-26, comprising: setting a P-wave sensing threshold; sensing atrial events in response to the cardiac electrical signal crossing a P-wave sensing threshold; setting a far-field R-wave sensing threshold; setting a far-field R-wave sensing window; sensing far-field R-waves in response to the cardiac electrical signal crossing the far-field R-wave sensing threshold during the far-field R-wave sensing window; and determining that the far field oversensing criteria are met based on at least the atrial events and far-field R-waves sensed during the atrial tachyarrhythmia.

28. The method of any of clauses 16-27, comprising generating pacing pulses according to a pacing therapy in response to detecting the atrial tachyarrhythmia.

29. The method of any of clauses 16-28, comprising transmitting an atrial tachyarrhythmia detection notification in response to detecting the atrial tachyarrhythmia.

30. A non-transitory, computer-readable storage medium storing a set of instructions which, when executed by a control circuit of a medical device, cause the medical device to: sense a cardiac electrical signal; detect an atrial tachyarrhythmia based on the sensed cardiac electrical signal; determine that far field oversensing criteria are met by the cardiac electrical signal during the detected atrial tachyarrhythmia; and detecting termination of the atrial tachyarrhythmia in response to at least the far field oversensing criteria being met.

31. A medical device comprising a sensing circuit configured to sense a cardiac electrical signal and a control circuit. The control circuit can be configured to detect an atrial tachyarrhythmia based on the sensed cardiac electrical signal, determine that far field oversensing criteria are met by the cardiac electrical signal during the detected atrial tachyarrhythmia, detect termination of the atrial tachyarrhythmia in response to at least the far field oversensing criteria being met and generate an output in response to detecting the termination of the atrial tachyarrhythmia. The medical device includes a memory configured to store the output generated by the control circuit.

32. The medical device of clause 31, wherein the control circuit is further configured to detect the termination of the atrial tachyarrhythmia by: starting a termination time interval in response to determining that the far field oversensing criteria are met; during the termination time interval, determining whether atrial tachyarrhythmia onset criteria are met based on at least the cardiac electrical signal; and detecting the termination of the atrial tachyarrhythmia in response to the termination time interval expiring and the atrial tachyarrhythmia onset criteria not being met.

33. The medical device of any of clauses 31-32, wherein the control circuit is further configured to determine that the far field oversensing criteria are met by identifying a plurality of sequences of atrial cycles, each of the plurality of sequences comprising at least two consecutive atrial cycles, classifying each of the plurality of sequences of atrial cycles as one of a far-field R-wave sequence or a non-far field R-wave sequence, determining that a threshold number of the plurality of sequences are classified as far-field R-wave sequences, and determining that the far field oversensing criteria are met when at least the threshold number of the plurality of sequences are classified as far-field R-wave sequences.

34. The medical device of clause 33, wherein the sensing circuit is further configured to set a P-wave sensing threshold and generate an atrial sensed event signal in response to the cardiac electrical signal crossing the P-wave sensing threshold and wherein the control circuit is further configured to classify a sequence of the plurality of sequences as a far field R-wave sequence in response to: determining that at least one peak amplitude of the cardiac electrical signal corresponding to one of at least three consecutive atrial sensed event signals is less than a far field R-wave peak amplitude limit, and at least one of: determining a pattern of alternating peak amplitudes of the cardiac electrical signal corresponding to at the least three consecutive atrial sensed event signals, or determining an atrial event interval between a consecutive pair of the at least three consecutive atrial sensed event signals that is greater than a predetermined long interval threshold.

35. The medical device of any of clauses 31-34, further comprising a pulse generator configured to generate atrial pacing pulses, wherein the control circuit is further configured to determine that a threshold number of atrial pacing pulses are generated during the detected atrial tachyarrhythmia; start a termination time interval in response to at least the threshold number of atrial pacing pulses being generated during the detected atrial tachyarrhythmia; during the termination time interval, determine that atrial tachyarrhythmia onset criteria are not met based on at least the far field oversensing criteria being met; and detect the termination of the atrial tachyarrhythmia in response to the termination time interval expiring and the atrial tachyarrhythmia onset criteria not being met.

36. The medical device of any of clauses 31-35, wherein the sensing circuit is further configured to: set a P-wave sensing threshold and generate an atrial sensed event signal in response to the cardiac electrical signal crossing the P-wave sensing threshold. The control circuit is further configured to determine atrial event intervals between consecutive atrial events comprising the atrial sensed event signals generated by the sensing circuit; during the detected atrial tachyarrhythmia, determine that a threshold number of the atrial event intervals are longer than a predetermined termination interval threshold; start a termination time interval in response to the threshold number of the atrial event intervals being longer than the predetermined termination interval threshold; during the termination time interval, determine that atrial tachyarrhythmia onset criteria are not met based on at least the far field oversensing criteria being met; and detect the termination of the atrial tachyarrhythmia in response to the termination time interval expiring and the atrial tachyarrhythmia onset criteria not being met.

37. The medical device of clause 36, further comprising a pulse generator configured to generate atrial pacing pulses, wherein the control circuit is configured to count an atrial event interval ending with an atrial pacing pulse generated by the pulse generator in the threshold number of the atrial event intervals that are longer than the predetermined termination interval threshold.

38. The medical device of any of clauses 31-37, wherein the sensing circuit is further configured to set a P-wave sensing threshold and generate an atrial sensed event signal in response to the cardiac electrical signal crossing the P-wave sensing threshold. The control circuit is further configured to: during the detected atrial tachyarrhythmia, determine a plurality of atrial event intervals comprising atrial sensed event signals generated by the sensing circuit; determine a count of the plurality of atrial event intervals that are longer than a predetermined termination interval threshold; start a termination time interval in response to one of: determining that the count of the plurality of atrial event intervals that are longer than the predetermined termination interval threshold is greater than a first threshold, or determining that the count of the plurality of atrial event intervals that are longer than the predetermined termination interval threshold is less than the first threshold and greater than a second threshold and that the far field oversensing criteria are met. The control circuit is further configured to, during the termination time interval, determine that atrial tachyarrhythmia onset criteria are not met based on at least the far field oversensing criteria being met and detect the termination of the atrial tachyarrhythmia in response to the termination time interval expiring and the atrial tachyarrhythmia onset criteria not being met.

39. The medical device of any of clauses 31-38, wherein the control circuit is further configured to detect the atrial tachyarrhythmia by: determining that atrial tachyarrhythmia onset criteria are met by the cardiac electrical signal; starting a detection time interval; determining that termination criteria are unmet by the cardiac electrical signal prior to an expiration of the detection time interval; and detecting the atrial tachyarrhythmia in response to the detection time interval expiring with the termination criteria being unmet.

40. The medical device of any of clauses 31-39, further comprising an accelerometer configured to sense an acceleration signal and wherein the control circuit is further configured to store a segment of the acceleration signal in the memory in response to detecting the atrial tachyarrhythmia.

41. The medical device of any of clauses 31-40, wherein the control circuit is further configured to detect the atrial tachyarrhythmia by: determining that atrial tachyarrhythmia onset criteria are met a first time by the cardiac electrical signal; starting a detection time interval in response to the atrial tachyarrhythmia onset criteria being met the first time; determining that termination criteria are met by the cardiac electrical signal prior to expiration of the detection time interval; starting a pending onset termination time interval with the detection time interval still running; determining that the atrial tachyarrhythmia onset criteria are met a second time by the cardiac electrical signal prior to the pending onset termination time interval expiring; and detecting the atrial tachyarrhythmia in response to expiration of the detection time interval.

42. The medical device of any of clauses 31-41, wherein the sensing circuit comprises a P-wave sensing channel configured to set a P-wave sensing threshold and sense atrial events in response to the cardiac electrical signal crossing a P-wave sensing threshold and a far-field R-wave sensing channel configured to set a far-field R-wave sensing threshold, set a far-field R-wave sensing window, and sense far-field R-waves in response to the cardiac electrical signal crossing the far-field R-wave sensing threshold during the far-field R-wave sensing window. The control circuit is further configured to determine that the far field oversensing criteria are met based on the atrial events sensed by the P-wave sensing channel and the far-field R-waves sensed by the far-field R-wave sensing channel.

43. The medical device of any of clauses 31-42, further comprising a pulse generator configured to generate pacing pulses according to a pacing therapy in response to the control circuit detecting the atrial tachyarrhythmia.

44. The medical device of any of clauses 31-43 further comprising a telemetry circuit configured to transmit an atrial tachyarrhythmia detection notification in response to the control circuit detecting the atrial tachyarrhythmia.

45. The medical device of any of clauses 31-44, further comprising a housing enclosing the sensing circuit and the control circuit, the housing comprising a pair of housing-based electrodes coupled to the sensing circuit for sensing the cardiac electrical signal.

46. The medical device of clause 45, further comprising a pulse generator configured to generate pacing pulses, wherein the pair of housing-based electrodes includes an electrode configured to deliver pacing pulses generated by the pulse generator to a His-Purkinje conduction system of a heart.

47. The medical device of clause 46, wherein the control circuit is further configured to control the pulse generator to generate pacing pulses delivered by the electrode according to a first pacing mode in response to detecting the atrial tachyarrhythmia, and control the pulse generator to generate pacing pulses delivered by the electrode according to a second pacing mode different than the first pacing mode in response to detecting termination of the atrial tachyarrhythmia.

48. A method performed by a medical device including sensing a cardiac electrical signal by a sensing circuit of the medical device, detecting an atrial tachyarrhythmia by a control circuit of the medical device based on the sensed cardiac electrical signal, determining that far field oversensing criteria are met by the cardiac electrical signal during the detected atrial tachyarrhythmia, detecting termination of the atrial tachyarrhythmia in response to at least the far field oversensing criteria being met, generating an output in response to detecting the termination of the atrial tachyarrhythmia, and storing the output in a memory of the medical device.

49. The method of clause 48, further comprising detecting the termination of the atrial tachyarrhythmia by: starting a termination time interval in response to determining that the far field oversensing criteria are met; during the termination time interval, determine if atrial tachyarrhythmia onset criteria are met based on at least the cardiac electrical signal; and detecting the termination of the atrial tachyarrhythmia in response to the termination time interval expiring and the atrial tachyarrhythmia onset criteria not being met.

50. The method of any of clauses 48-49, wherein determining that the far field oversensing criteria are met further comprises: identifying a plurality of sequences of atrial cycles, each of the plurality of sequences comprising at least two consecutive atrial cycles; classifying each of the plurality of sequences as one of a far-field R-wave sequence or a non-far field R-wave sequence; determining that a threshold number of the plurality of sequences are classified as far-field R-wave sequences; and determining that the far field oversensing criteria are met when at least the threshold number of the plurality of sequences are classified as far-field R-wave sequences.

51. The method of clause 50, further comprising: setting a P-wave sensing threshold; generating an atrial sensed event signal in response to the cardiac electrical signal crossing the P-wave sensing threshold; and classifying a sequence of the plurality of sequences as a far field R-wave sequence in response to determining that at least one maximum peak amplitude of the cardiac electrical signal corresponding to one of at least three consecutive atrial sensed event signals is less than a far field R-wave peak amplitude limit, and at least one of: determining a pattern of alternating peak amplitudes of the cardiac electrical signal corresponding to the at least three consecutive atrial sensed event signals generated by the sensing circuit, or determining an atrial event interval between a consecutive pair of the at least three consecutive atrial sensed event signals that is greater than a predetermined long interval threshold.

52. The method of any of clauses 48-51, further comprising generating atrial pacing pulses; determining that a threshold number of atrial pacing pulses are generated during the detected atrial tachyarrhythmia; starting a termination time interval in response to the threshold number of atrial pacing pulses being generated during the detected atrial tachyarrhythmia; during the termination time interval, determining that atrial tachyarrhythmia onset criteria are not met based on at least the far field oversensing criteria being met; and detecting the termination of the atrial tachyarrhythmia in response to the termination time interval expiring and the atrial tachyarrhythmia onset criteria not being met.

53. The method of any of clauses 48-52, further comprising: setting a P-wave sensing threshold; generating an atrial sensed event signal in response to the cardiac electrical signal crossing the P-wave sensing threshold; determining atrial event intervals between consecutive atrial events comprising the atrial sensed event signals generated by the sensing circuit; during the detected atrial tachyarrhythmia, determining that a threshold number of the atrial event intervals are longer than a predetermined termination interval threshold; starting a termination time interval in response to the threshold number of the atrial event intervals being longer than the predetermined termination interval threshold; during the termination time interval, determining that atrial tachyarrhythmia onset criteria are not met based on at least the far field oversensing criteria being met; and detecting the termination of the atrial tachyarrhythmia in response to the termination time interval expiring and the atrial tachyarrhythmia onset criteria not being met.

54. The method of clause 53, further comprising: generating atrial pacing pulses; and counting an atrial event interval ending with an atrial pacing pulse in the threshold number of the atrial event intervals that are longer than the predetermined termination interval threshold.

55. The method of any of clauses 48-54, further comprising: setting a P-wave sensing threshold; generating an atrial sensed event signal in response to the cardiac electrical signal crossing the P-wave sensing threshold; during the detected atrial tachyarrhythmia, determining a plurality of atrial event intervals comprising atrial sensed event signals; determining a count of the plurality of atrial event intervals that are longer than a predetermined termination interval threshold; starting the termination time interval in response to one of: determining that the count of the plurality of atrial event intervals that are longer than the predetermined termination interval threshold is greater than a first threshold, or determining that the count of the plurality of atrial event intervals that are longer than the predetermined termination interval threshold is less than the first threshold and greater than a second threshold and that the far field oversensing criteria are met; and during the termination time interval, determining that atrial tachyarrhythmia onset criteria are not met based on at least the far field oversensing criteria being met; and detecting the termination of the atrial tachyarrhythmia in response to the termination time interval expiring and the atrial tachyarrhythmia onset criteria not being met.

56. The method of any of clauses 48-55, wherein detecting the atrial tachyarrhythmia comprises: determining that the atrial tachyarrhythmia onset criteria are met by the cardiac electrical signal; starting a detection time interval; determining that termination criteria are unmet by the cardiac electrical signal prior to an expiration of the detection time interval; and detecting the atrial tachyarrhythmia in response to the detection time interval expiring with the termination criteria being unmet.

57. The method of clause 56, further comprising sensing an acceleration signal and storing a segment of the acceleration signal in the memory in response to detecting the atrial tachyarrhythmia.

58. The method of any of clauses 48-57 further comprising detecting the atrial tachyarrhythmia by: determining that atrial tachyarrhythmia onset criteria are met a first time by the cardiac electrical signal; starting a detection time interval in response to the atrial tachyarrhythmia onset criteria being met the first time; determining that termination criteria are met by the cardiac electrical signal prior to expiration of the detection time interval; starting a pending onset termination time interval with the detection time interval still running; determining that the atrial tachyarrhythmia onset criteria are met a second time by the cardiac electrical signal prior to the pending onset termination time interval expiring; and detecting the atrial tachyarrhythmia in response to expiration of the detection time interval.

59. The method of any of clauses 48-58, further comprising: setting a P-wave sensing threshold; sensing atrial events in response to the cardiac electrical signal crossing a P-wave sensing threshold; setting a far-field R-wave sensing threshold; setting a far-field R-wave sensing window; sensing far-field R-waves in response to the cardiac electrical signal crossing the far-field R-wave sensing threshold during the far-field R-wave sensing window; and determining that the far field oversensing criteria are met based on the atrial events sensed by the P-wave sensing channel and the far-field R-waves sensed by the far-field R-wave sensing channel.

60. The method of any of clauses 48-59, further comprising generating pacing pulses according to a pacing therapy in response to detecting the atrial tachyarrhythmia.

61. The method of any of clauses 48-60, further comprising transmitting an atrial tachyarrhythmia detection notification in response to detecting the atrial tachyarrhythmia.

62. The method of any of clauses 48-61, further comprising: generating pacing pulses for delivery by an electrode configured to deliver pacing pulses to a His-Purkinje conduction system of a heart according to a first pacing mode in response to detecting the atrial tachyarrhythmia; and generating pacing pulses delivered by the electrode according to a second pacing mode different than the first pacing mode in response to detecting termination of the atrial tachyarrhythmia.

63. A non-transitory, computer-readable storage medium storing a set of instructions which, when executed by a control circuit of a medical device, cause the medical device to: sense a cardiac electrical signal; detect an atrial tachyarrhythmia based on the sensed cardiac electrical signal; determine that far field oversensing criteria are met by the cardiac electrical signal during the detected atrial tachyarrhythmia; detect termination of the atrial tachyarrhythmia in response to at least the far field oversensing criteria being met; generate an output in response to detecting the termination of the atrial tachyarrhythmia; and store the output in a memory of the medical device.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes a medical device and techniques for detecting atrial tachyarrhythmia. The medical device is configured to sense a cardiac electrical signal, which may be sensed from an atrial location and may also be referred to herein as an "atrial electrical signal." The atrial electrical signal generally includes P-waves, which are attendant to intrinsic atrial depolarizations. While sensed from an atrial location, the atrial electrical signal may include FFRWs attendant to ventricular depolarizations occurring in the ventricle, away from the atrial sensing site. According to the techniques disclosed herein, the medical device is configured to analyze the atrial electrical signal for detecting an atrial tachyarrhythmia while avoiding false detection of AT/AF or failing to detect termination of the AT/AF due to oversensing of FFRWs as atrial P-waves.

Figure 1A:
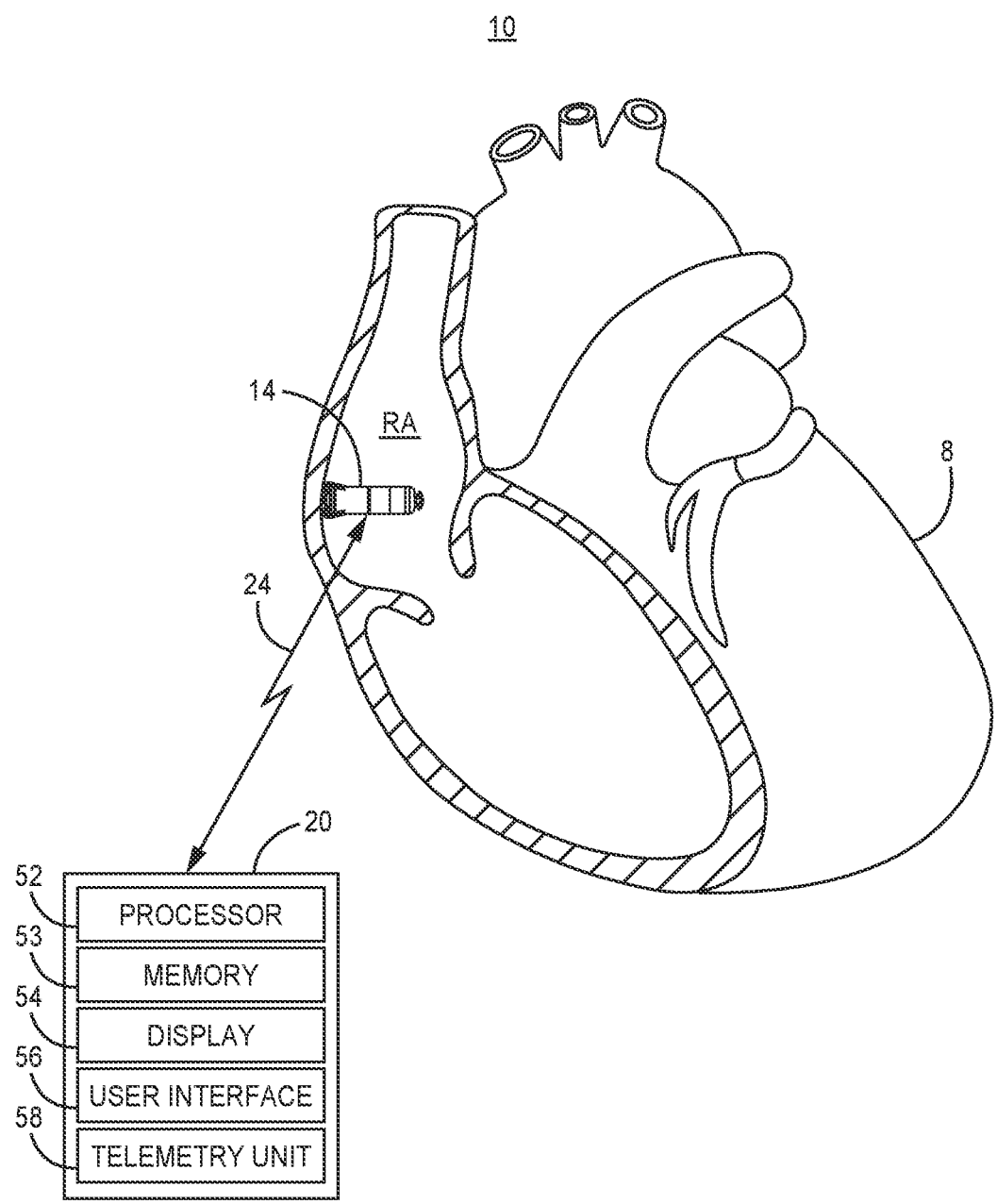
FIG. 1A is a conceptual diagram illustrating an implantable medical device (IMD) system that may be used to sense cardiac signals and perform AT/AF detection according to the techniques disclosed herein.
Figure 2:
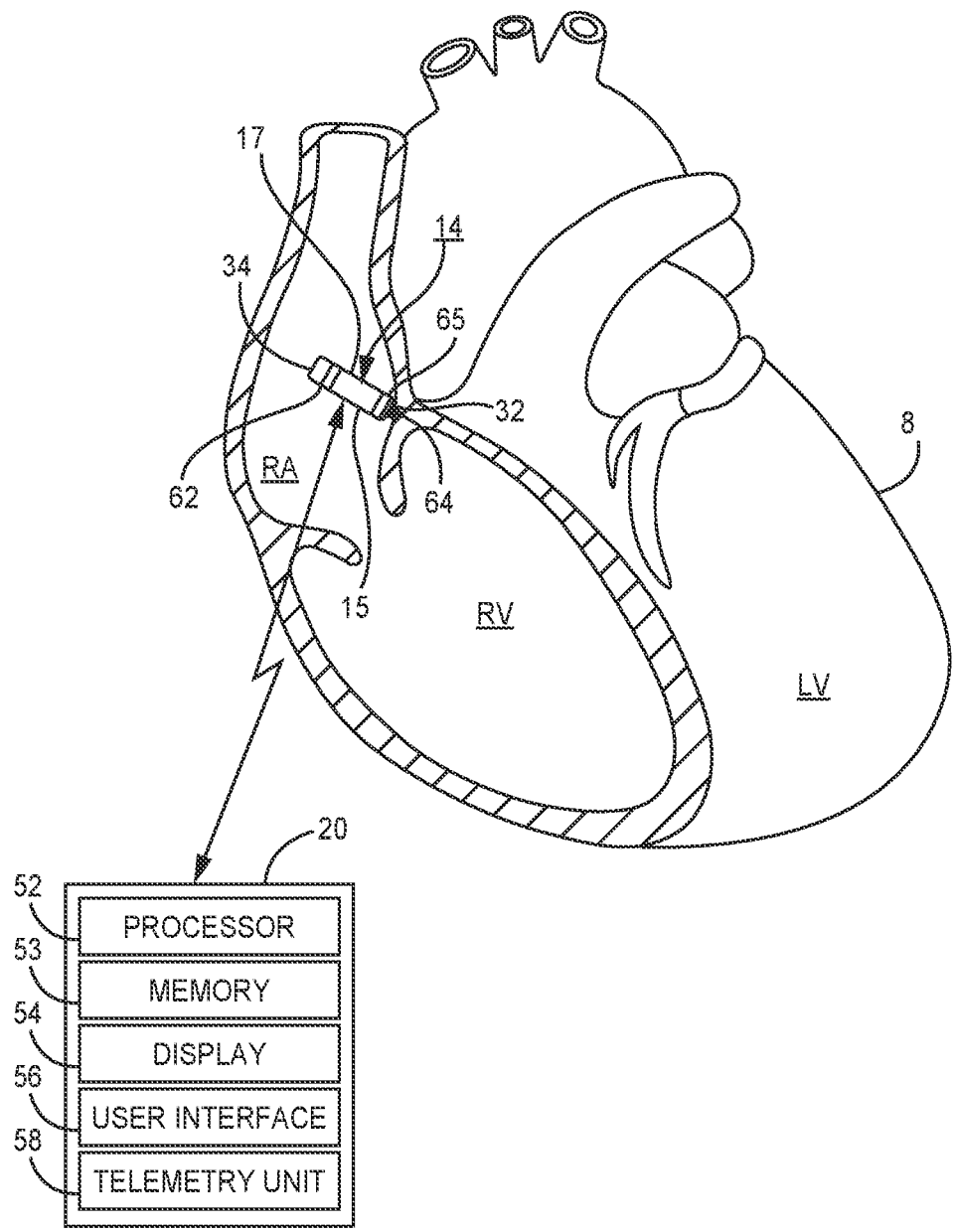
FIG. 2 is a conceptual diagram of a leadless pacemaker implanted in the right atrium in a different position than the position shown in FIG. 1A.

FIG. 1A is a conceptual diagram illustrating an implantable medical device (IMD) system 10 that may be used to sense cardiac signals and provide AT/AF detection. IMD system 10 is shown including pacemaker 14, shown implanted within the right atrium (RA). Pacemaker 14 may be a transcatheter leadless pacemaker which is implantable wholly within a heart chamber, e.g., wholly within the RA of heart 8 for sensing cardiac signals and delivering atrial pacing pulses from within the atrium. Pacemaker 14 may be implanted at other locations within or on the RA, including epicardial locations, different than the lateral endocardial wall location as shown. An alternative implant location of pacemaker 14 is shown in FIG. 2, as an example.

Pacemaker 14 includes housing-based electrodes for sensing cardiac electrical signals and delivering pacing pulses. Pacemaker 14 may include cardiac electrical signal sensing circuitry configured to sense intrinsic atrial P-waves attendant to the depolarization of the atrial myocardium and a pulse generator for generating and delivering an atrial pacing pulse in the absence of a sensed intrinsic atrial P-wave. In some examples, the cardiac electrical sensing circuit is configured to sense FFRWs attendant to the depolarization of the ventricular myocardium.

In some examples, pacemaker 14 may include an accelerometer enclosed within or on the housing of the pacemaker. The accelerometer is subjected to acceleration forces due to cardiac and blood motion. The acceleration signal generated by the accelerometer may include signals that correspond to ventricular contraction and atrial contraction, which may be used for monitoring the heart rhythm and controlling pacing therapy in some examples. The acceleration signal sensed by the accelerometer may include acceleration signals due to patient body motion, e.g., during physical activity, in addition to acceleration signals due to cardiac motion. The acceleration signal may be used by processing circuitry included in the pacemaker 14 for determining a patient physical activity metric. The rate of atrial pacing pulses generated and delivered by pacemaker 14 may be adjusted based on the patient physical activity metric determined from the accelerometer signal for providing rate response pacing in some examples.

Pacemaker 14 may be capable of bidirectional wireless communication with an external device 20 for programming sensing and pacing control parameters, which may include control parameters used for sensing the cardiac electrical signal, the acceleration signal, control parameters used for detecting AT/AF and providing an output or response to an AT/AF detection, and control parameters used for controlling the delivery of pacing pulses by pacemaker 14, e.g., atrial pacing pulses and/or ventricular conduction system pacing pulses in some examples. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in an implantable medical device, e.g., pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 by a user interacting with external device 20.

External device 20 may include a processor 52, memory 53, display unit 54, user interface 56 and telemetry unit 58. Processor 52 controls external device operations and processes data and signals received from pacemaker 14. Display unit 54 may generate a display, which may include a graphical user interface, of data and information relating to pacemaker functions to a user for reviewing pacemaker operation and programmed parameters as well as cardiac electrical signals, accelerometer signals, or other physiological data that may be acquired by pacemaker 14 and transmitted to external device 20 during an interrogation session. For example, pacemaker 14 may generate an output for transmission to external device 20 relating to detected AT/AF episodes. Transmitted data may include a recording of a cardiac electrical signal sensed by pacemaker sensing circuitry including markers indicating sensed atrial event signals and AT/AF detection, a date and time stamp of an AT/AF detection, AT/AF episode duration, AT/AF burden or the like.

User interface 56 may include a mouse, touch screen, keypad or the like to enable a user to interact with external device 20 to initiate a telemetry session with pacemaker 14 for retrieving data from and/or transmitting data to the pacemaker 14, including programmable parameters for controlling AT/AF detection. In some examples, telemetry unit 58 includes a transceiver and antenna configured for bidirectional communication with a telemetry circuit included in pacemaker 14 and is configured to operate in conjunction with processor 52 for sending and receiving data relating to pacemaker functions via communication link 24.

Telemetry unit 58 may establish a wireless bidirectional communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24. In other examples external device 20 and pacemaker 14 may be configured to communicate using a distance telemetry algorithm and circuitry that does not require the use of a programming head and does not require user intervention to maintain a communication link.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to view data relating to sensing cardiac signals, AT/AF detection and pacing operations performed by pacemaker 14.

Figure 1B:
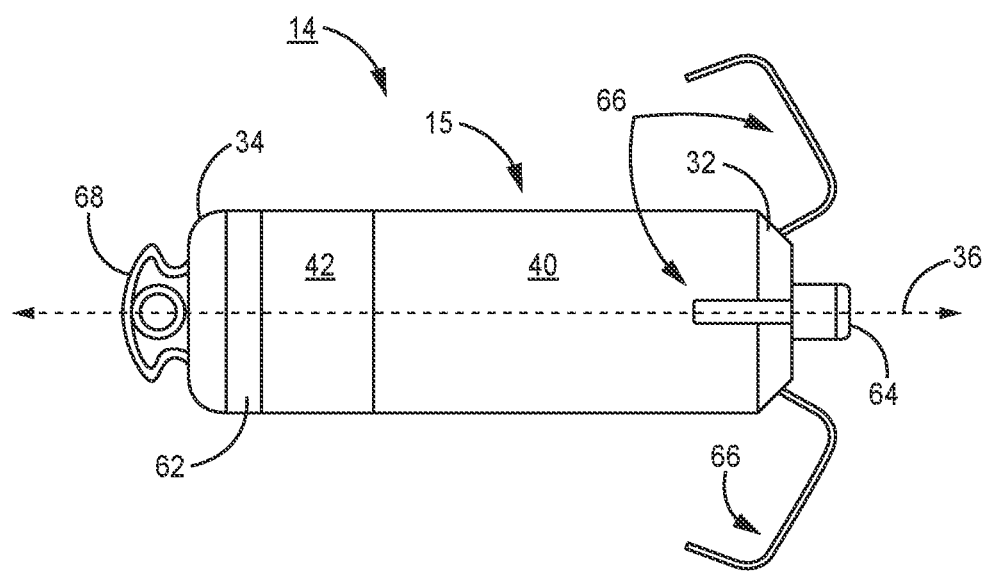
FIG. 1B is a conceptual diagram of the transcatheter leadless pacemaker of FIG. 1 according to one example.

FIG. 1B is a conceptual diagram of the transcatheter leadless pacemaker 14 of FIG. 1A according to one example. Pacemaker 14 includes a housing 15 that may include a control electronics subassembly 40 and a battery subassembly 42, which provides power to the control electronics subassembly 40. Pacemaker 14 includes electrodes 62 and 64 spaced apart along the housing 15 of pacemaker 14 for sensing cardiac electrical signals and delivering pacing pulses. Electrode 64 is shown as a tip electrode extending from a distal end 32 of pacemaker 14, and electrode 62 is shown as a ring electrode circumscribing the lateral sidewall 17 of housing 15, along a mid-portion of housing 15. In the example shown, electrode 62 is shown adjacent proximal end 34 of housing 15. Distal end 32 is referred to as "distal" in that it is expected to be the leading end of pacemaker 14 as pacemaker 14 is advanced through a delivery tool, such as a catheter, and placed against a targeted pacing site.

Electrodes 62 and 64 form an anode and cathode pair for bipolar cardiac pacing and sensing. In alternative embodiments, pacemaker 14 may include two or more ring electrodes, two tip electrodes, and/or other types of electrodes exposed along pacemaker housing 15 for delivering electrical stimulation to heart 8 and sensing cardiac electrical signals. Electrodes 62 and 64 may be, without limitation, titanium, platinum, iridium or alloys thereof and may include a low polarizing coating, such as titanium nitride, iridium oxide, ruthenium oxide, platinum black, among others. Electrodes 62 and 64 may be positioned at locations along pacemaker 14 other than the locations shown and may include ring, button, hemispherical, hook, helical or other types of electrodes.

Housing 15 is formed from a biocompatible material, such as a stainless steel or titanium alloy. In some examples, the housing 15 may include an insulating coating. Examples of insulating coatings include parylene, urethane, PEEK, or polyimide, among others. The entirety of the housing 15 may be insulated, but only electrodes 62 and 64 uninsulated. Electrode 64 may serve as a cathode electrode and be coupled to internal circuitry, e.g., a pacing pulse generator and cardiac electrical signal sensing circuitry, enclosed by housing 15 via an electrical feedthrough crossing housing 15. Electrode 62 may be formed as a conductive portion of housing 15 defining a ring electrode that is electrically isolated from the other portions of the housing 15 as generally shown in FIG. 1B. In other examples, the entire periphery of the housing 15 may function as an electrode that is electrically isolated from tip electrode 64, instead of providing a localized ring electrode such as electrode 62. Electrode 62 formed along an electrically conductive portion of housing 15 serves as a return anode during pacing and sensing.

Control electronics subassembly 40 houses the electronics for sensing cardiac signals, detecting arrhythmias, producing pacing pulses and controlling therapy delivery and other functions of pacemaker 14 as described herein. A motion sensor implemented as an accelerometer may optionally be enclosed within housing 15 in some examples. The accelerometer may provide a signal to a processor included in control electronics subassembly 52 for signal processing and analysis for use in sensing atrial and ventricular mechanical events, detecting AT/AF and may be used for determining a patient physical activity metric for use in controlling rate response cardiac pacing.

Pacemaker 14 may include features for facilitating deployment and fixation of pacemaker 14 at an implant site. For example, pacemaker 14 may include a set of fixation tines 66 to secure pacemaker 14 to patient tissue, e.g., by actively engaging with the atrial pectinate muscle or atrial endocardial tissue. Fixation tines 66 are configured to anchor pacemaker 14 to position electrode 64 in operative proximity to a targeted tissue for delivering therapeutic electrical stimulation pulses. Numerous types of active and/or passive fixation members may be employed for anchoring or stabilizing pacemaker 14 in an implant position.

Pacemaker 14 may optionally include a delivery tool interface 68. Delivery tool interface 68 may be located at the proximal end 34 of pacemaker 14 and is configured to connect to a delivery device, such as a catheter, used to position pacemaker 14 at an implant site during an implantation procedure, for example within or on an atrial chamber.

FIG. 2 is a conceptual diagram of pacemaker 14 implanted in an alternative location within the RA for sensing atrial electrical signals and for delivering cardiac pacing pulses. Pacemaker 14 may be positioned within the RA for providing ventricular pacing via the native ventricular conduction system, which includes the His bundle, the right and left bundle branches and the Purkinje fibers and may be referred to as the "His-Purkinje system." Pacemaker 14 includes distal tip electrode 64 extending from a distal end 32 of the pacemaker housing 15 as described above. In FIG. 2, pacemaker 14 is shown implanted in the RA of the patient's heart to place distal tip electrode 64 for delivering pacing pulses to or in the area of the His bundle.

For example, the distal tip electrode 64 may be a tissue piercing electrode that can be inserted into the inferior end of the interatrial septum, beneath the AV node and near the tricuspid valve annulus to position tip electrode 64 in, along or proximate to the His bundle. Distal tip electrode 64 may be a helical electrode, as shown in this example, providing fixation to anchor the pacemaker 14 at the implant position as well as deliver pacing pulses. In other examples, pacemaker 14 may include a fixation member that includes one or more tines, hooks, barbs, helices or other fixation member(s) that anchor the distal end 32 of the pacemaker 14 at the implant site. Another example of a pacemaker that may be configured to operate according to the techniques disclosed herein and is configured for delivering pacing to the His-Purkinje system is generally disclosed in U.S. Patent Application Publication No. 2019/0083800 A1 (Yang, et al., granted as U.S. Pat. No. 11,478,653), incorporated herein by reference in its entirety.

A portion of the distal tip electrode 64 may be electrically insulated such that only the most distal end of tip electrode 64, furthest from housing distal end 32, is exposed to provide targeted pacing at a tissue site that includes a portion of the His bundle. One or more housing-based electrodes 62 and 65 may be carried on the surface of the housing 15 of pacemaker 14. Electrodes 62 and 65 are shown as ring electrodes circumscribing the lateral sidewall 17 of pacemaker housing 15. Lateral sidewall 17 extends from distal end 32 to proximal end 34. In other examples, a return anode electrode used in sensing and pacing may be positioned on housing proximal end 34. Pacing of the His-Purkinje system may be achieved using the distal tip electrode 32 as the cathode electrode and either of the housing-based electrodes 62 or 65 as the return anode.

Cardiac electrical signals produced by heart 8 may be sensed by pacemaker 14 using a sensing electrode pair selected from electrodes 62, 64 and 65. For example, a cardiac electrical signal may be sensed using distal tip electrode 64 and distal housing-based electrode 65 or distal tip electrode 64 and proximal housing-based electrode 62. A second cardiac electrical signal may be sensed using electrodes 65 and 62. In other examples, a single cardiac electrical signal may be sensed using a single electrode pair selected from electrodes 62, 64 and 65. The cardiac electrical signals sensed by pacemaker 14 may be processed and analyzed by sensing and control circuitry included in pacemaker 14, e.g., as described below in conjunction with FIG. 4, for detecting the onset and termination of AT/AF according to the techniques disclosed herein. In some examples, atrial P-waves (and FFRWs) may be sensed from a signal received via electrodes 65 and 64 and/or atrial pacing pulses may be delivered via electrodes 65 and 64. Atrial synchronous or asynchronous ventricular pacing pulses may be delivered via electrodes 62 and 64 to capture at least a portion of the His-Purkinje system.

Figure 3A:
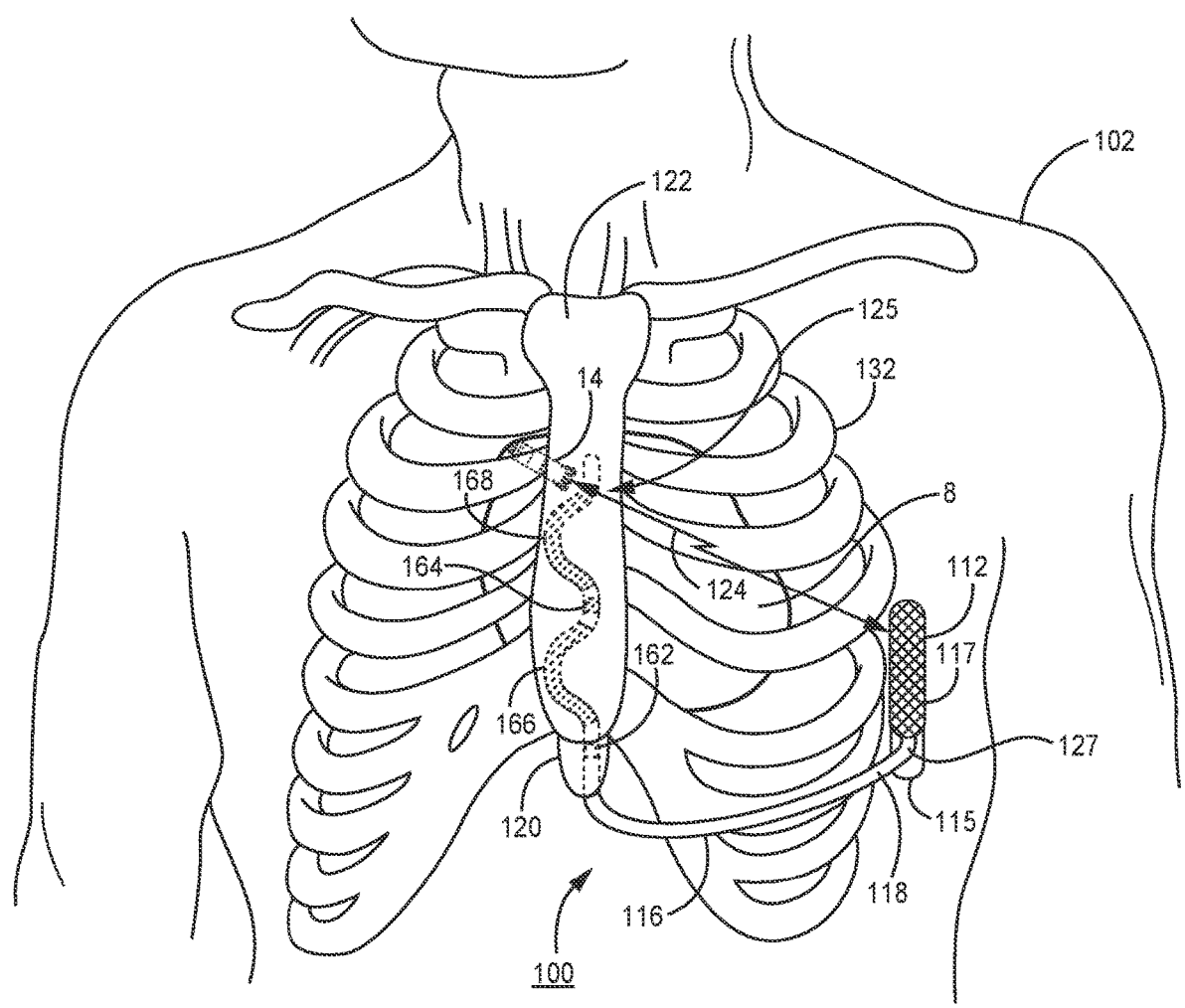
FIGS. 3A-3C are conceptual diagrams of a patient implanted with an IMD system that may include a leadless atrial pacemaker and an implantable cardioverter defibrillator (ICD) according to another example.
Figure 3B:
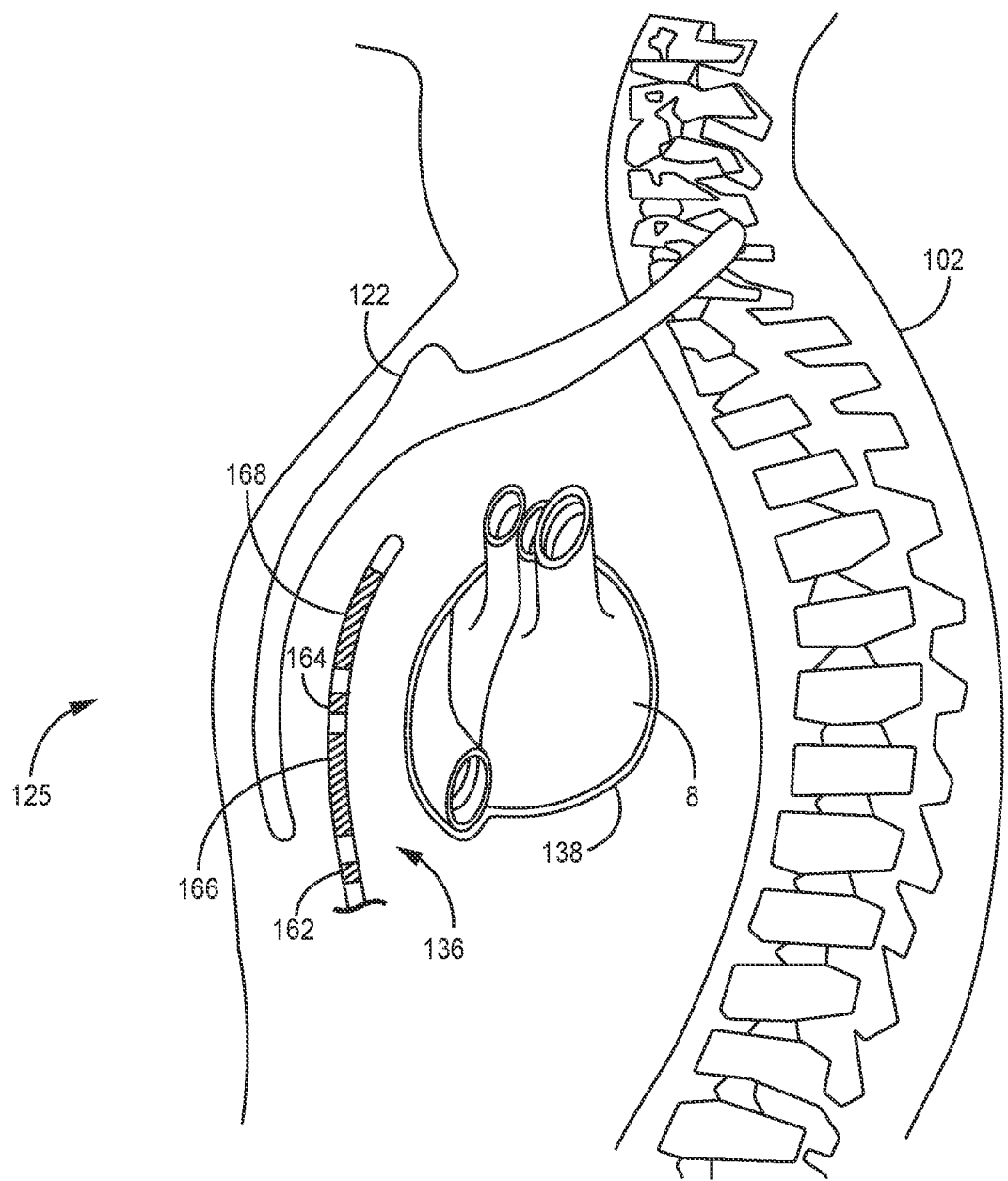
Figure 3C:
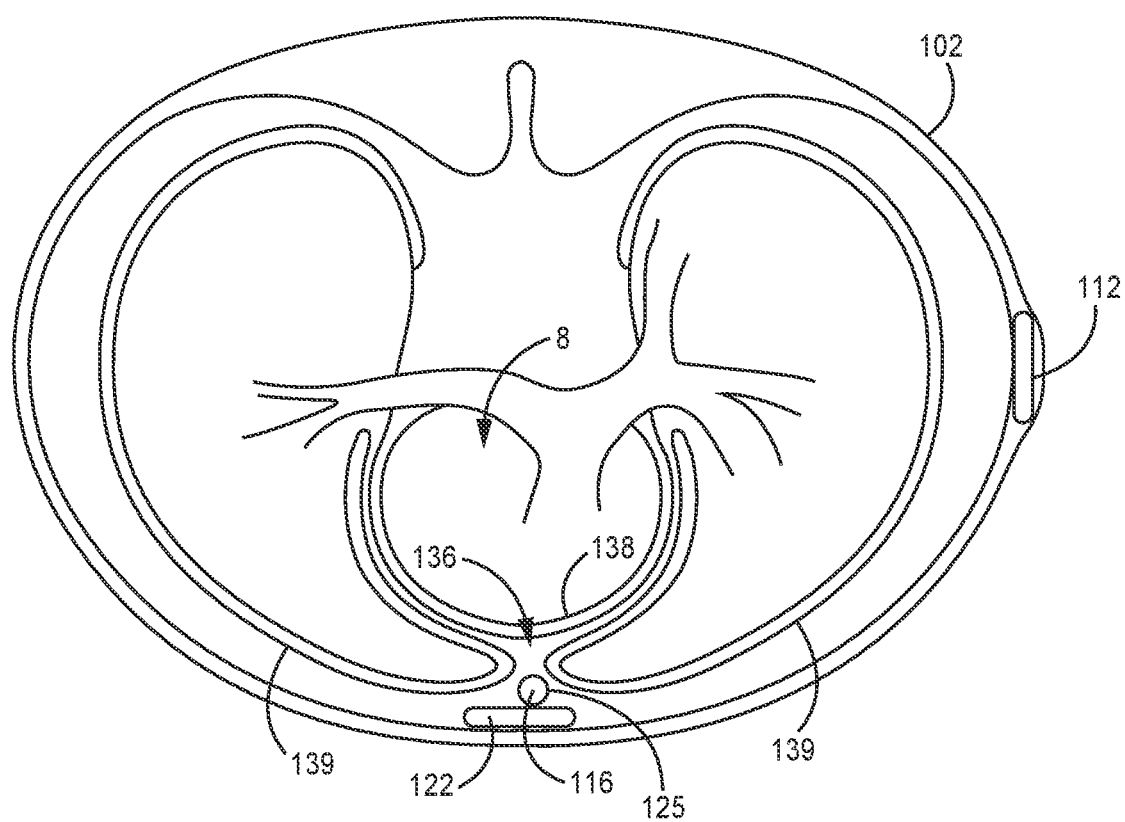

FIGS. 3A-3C are conceptual diagrams of a patient 102 implanted with an IMD system 100 that may include pacemaker 14 according to another example. FIG. 3A is a front view of patient 102 implanted with IMD system 100. FIG. 3B is a side view of patient 102 implanted with IMD system 100. FIG. 3C is a transverse view of patient 102 implanted with IMD system 100. In this example, IMD system 100 includes an ICD 112 connected to an extra-cardiovascular electrical stimulation and sensing lead 116. In the implant configuration shown, lead 116 is implanted at least partially underneath sternum 122 of patient 102. Lead 116 extends subcutaneously or submuscularly from ICD 112 toward xiphoid process 120 and at a location near xiphoid process 120 bends or turns and extends superiorly within anterior mediastinum 136 (see FIGS. 3B and 3C) in a substernal position. The path of extra-cardiovascular lead 116 may depend on the location of ICD 112, the arrangement and position of electrodes carried by the lead body 118, and/or other factors. The techniques disclosed herein are not limited to a particular path of lead 116 or final locations of electrodes carried by lead body 118.

Anterior mediastinum 136 may be viewed as being bounded laterally by pleurae 139, posteriorly by pericardium 138, and anteriorly by sternum 122. The distal portion 125 of lead 116 may extend along the posterior side of sternum 122 substantially within the loose connective tissue and/or substernal musculature of anterior mediastinum 136. A lead implanted such that the distal portion 125 is substantially within anterior mediastinum 136, or within a pleural cavity or more generally within the thoracic cavity, may be referred to as a "substernal lead."

In the example illustrated in FIGS. 3A-3C, the distal portion 125 of lead 116 is located substantially centered under sternum 122. In other instances, however, lead 116 may be implanted such that the distal portion 125 may be offset laterally from the center of sternum 122. In some instances, lead 116 may extend laterally such that distal portion 125 is underneath/below the ribcage 132 in addition to or instead of sternum 122. In other examples, the distal portion 125 of lead 116 may be implanted in other extra-cardiac, intra-thoracic locations, including the pleural cavity or around the perimeter of and adjacent to or within the pericardium 138 of heart 8.

Lead 116 is shown in this example as an extra-cardiovascular lead implanted in a substernal location. In other examples, however, lead 116 may be implanted outside the ribcage and sternum, e.g., in a suprasternal location or adjacent sternum 122, over ribcage 132. While ICD 112 is shown coupled to a non-transvenous lead 116 positioned in an extra-cardiovascular location, in other examples ICD 112 may be coupled to a transvenous lead that positions electrodes within a blood vessel but may remain outside the heart in an extra-cardiac location. For example, a transvenous medical lead may be advanced along a venous pathway to position electrodes within the internal thoracic vein (ITV), an intercostal vein, the superior epigastric vein, or the azygos, hemiazygos, or accessory hemiazygos veins, as examples.

ICD 112 includes a housing 115 that forms a hermetic seal that protects internal components of ICD 112. The housing 115 of ICD 112 may be formed of a conductive material, such as titanium or titanium alloy. The housing 115 may function as an electrode (sometimes referred to as a "can" electrode). Housing 115 may be used as an active can electrode for use in delivering CV/DF shocks or other high voltage pulses delivered using a high voltage therapy circuit. In other examples, housing 115 may be available for use in delivering unipolar, low voltage cardiac pacing pulses and/or for sensing cardiac electrical signals in combination with electrodes carried by lead 116. In other instances, the housing 115 of ICD 112 may include a plurality of electrodes on an outer portion of the housing. The outer portion(s) of the housing 115 functioning as an electrode(s) may be coated with a material, such as titanium nitride, e.g., for reducing post-stimulation polarization artifact.

ICD 112 includes a connector assembly 117 (also referred to as a connector block or header) that includes electrical feedthroughs crossing housing 115 to provide electrical connections between conductors extending within the lead body 118 of lead 116 and electronic components included within the housing 115 of ICD 112. Housing 115 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 116 includes an elongated lead body 118 having a proximal end 127 that includes a lead connector (not shown) configured to be connected to ICD connector assembly 117 and a distal portion 125 that includes one or more electrodes. In the example illustrated in FIGS. 3A-3C, the distal portion 125 of lead body 118 includes defibrillation electrodes 166 and 168 and pace/sense electrodes 162 and 164. In some cases, defibrillation electrodes 166 and 168 may together form a defibrillation electrode in that they may be configured to be activated concurrently. Alternatively, defibrillation electrodes 166 and 168 may form separate defibrillation electrodes in which case each of the electrodes 166 and 168 may be activated independently.

Electrodes 166 and 168 (and in some examples housing 115) are referred to herein as defibrillation electrodes because they may be utilized, individually or collectively, for delivering high voltage stimulation therapy (e.g., cardioversion or defibrillation shocks). Electrodes 166 and 168 may be elongated coil electrodes and generally have a relatively high surface area for delivering high voltage electrical stimulation pulses compared to pacing and sensing electrodes 162 and 164. However, electrodes 166 and 168 and housing 115 may also be utilized to provide pacing functionality, sensing functionality, or both pacing and sensing functionality in addition to or instead of high voltage stimulation therapy. In this sense, the use of the term "defibrillation electrode" herein should not be considered as limiting the electrodes 166 and 168 for use in only high voltage cardioversion/defibrillation shock therapy applications. For example, either of electrodes 166 and 168 may be used as a sensing electrode in a sensing vector for sensing cardiac electrical signals and determining a need for an electrical stimulation therapy.

Electrodes 162 and 164 are relatively smaller surface area electrodes which are available for use in sensing electrode vectors for sensing cardiac electrical signals and may be used for delivering relatively low voltage pacing pulses in some configurations, e.g., for delivering rate response pacing pulses. Electrodes 162 and 164 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 162 and 164 may provide only pacing functionality, only sensing functionality or both.

ICD 112 may obtain cardiac electrical signals corresponding to electrical activity of heart 8 via a combination of sensing electrode vectors that include combinations of electrodes 162, 164, 166 and/or 168. In some examples, housing 115 of ICD 112 is used in combination with one or more of electrodes 162, 164, 166 and/or 168 in a sensing electrode vector. In the example illustrated in FIGS. 3A-3C, electrode 162 is located proximal to defibrillation electrode 166, and electrode 164 is located between defibrillation electrodes 166 and 168. One, two or more pace/sense electrodes (or none) may be carried by lead body 118 and may be positioned at different locations along distal lead portion 125 than the locations shown. Electrodes 162 and 164 are illustrated as ring electrodes; however, electrodes 162 and 164 may comprise any of a number of different types of electrodes, including ring electrodes, short coil electrodes, hemispherical electrodes, directional electrodes, segmented electrodes, or the like.

Electrical conductors (not illustrated) extend through one or more lumens of the elongated lead body 118 of lead 116 from the lead connector at the proximal lead end 127 to electrodes 162, 164, 166, 168. Elongated electrical conductors contained within the lead body 118, which may be separate respective insulated conductors within the lead body 118, are each electrically coupled with respective defibrillation electrodes 166 and 168 and pace/sense electrodes 162 and 164. The respective conductors electrically couple the electrodes 162, 164, 166, 168 to circuitry, such as a therapy delivery circuit and/or a sensing circuit, of ICD 112 via connections in the connector assembly 117, including associated electrical feedthroughs crossing housing 115. The electrical conductors transmit therapy from a therapy delivery circuit within ICD 112 to one or more of defibrillation electrodes 166 and 168 and/or pace/sense electrodes 162 and 164 and transmit cardiac electrical signals from the patient's heart 8 from one or more of electrodes 162, 164, 166, 168 to the sensing circuit within ICD 112.

The lead body 118 of lead 116 may be formed from a non-conductive material, including silicone, polyurethane, fluoropolymers, mixtures thereof, and/or other appropriate materials, and shaped to form one or more lumens within which the one or more conductors extend. Lead body 118 may be tubular or cylindrical in shape. In other examples, the distal portion 125 (or all of) the elongated lead body 118 may have a flat, ribbon or paddle shape. Lead body 118 may be formed having a preformed distal portion 125 that is generally straight, curving, bending, serpentine, undulating or zig-zagging. In the example shown, lead body 118 includes a curving distal portion 125 having two "C" shaped curves, which together may resemble the Greek letter epsilon, "ε." The techniques disclosed herein are not limited to any particular lead body design, however. In other examples, lead body 118 is a flexible elongated lead body without any pre-formed shape, bends or curves.

ICD 112 analyzes the cardiac electrical signals received from one or more sensing electrode vectors to monitor for abnormal rhythms, such as bradycardia, ventricular tachycardia (VT) or ventricular fibrillation (VF). ICD 112 may analyze the heart rate and morphology of the cardiac electrical signals to monitor for tachyarrhythmia in accordance with any of a number of tachyarrhythmia detection techniques. ICD 112 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 112 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 112 may deliver one or more CV/DF shocks via one or both of defibrillation electrodes 166 and 168 and/or housing 115. ICD 112 may generate and deliver other types of electrical stimulation pulses such as post-shock pacing pulses, asystole pacing pulses, or bradycardia pacing pulses using a pacing electrode vector that includes one or more of the electrodes 162, 164, 166, 168 and the housing 115 of ICD 112.

ICD 112 is shown implanted subcutaneously on the left side of patient 102 along the ribcage 132. ICD 112 may, in some instances, be implanted between the left posterior axillary line and the left anterior axillary line of patient 102. ICD 112 may, however, be implanted at other subcutaneous or submuscular locations in patient 102. For example, ICD 112 may be implanted in a subcutaneous pocket in the pectoral region. In this case, lead 116 may extend subcutaneously or submuscularly from ICD 112 toward the manubrium of sternum 22 and bend or turn and extend inferiorly from the manubrium to the desired location subcutaneously, submuscularly, substernally, over or beneath the ribcage 132. In yet another example, ICD 112 may be placed abdominally.

IMD system 100 is shown including pacemaker 14, shown conceptually as being implanted within the right atrium in FIG. 3A. ICD 112 and pacemaker 14 may be configured for bi-directional communication via telemetry link 124. Pacemaker 14 may be configured to transmit an AT/AF detection signal for receipt by ICD 112. ICD 112 may be configured to respond to a transmitted AT/AF detection signal by withholding a VT/VF detection and/or withhold a VT/VF therapy, e.g., a shock therapy or anti-tachycardia pacing. In other examples, ICD 112 may deliver a cardioversion shock in response to receiving an AT/AF notification signal transmitted by pacemaker 14 indicating an AT/AF episode is being detected. ICD 112 may deliver cardioversion therapy in an attempt to terminate the AT/AF episode.

Figure 4:
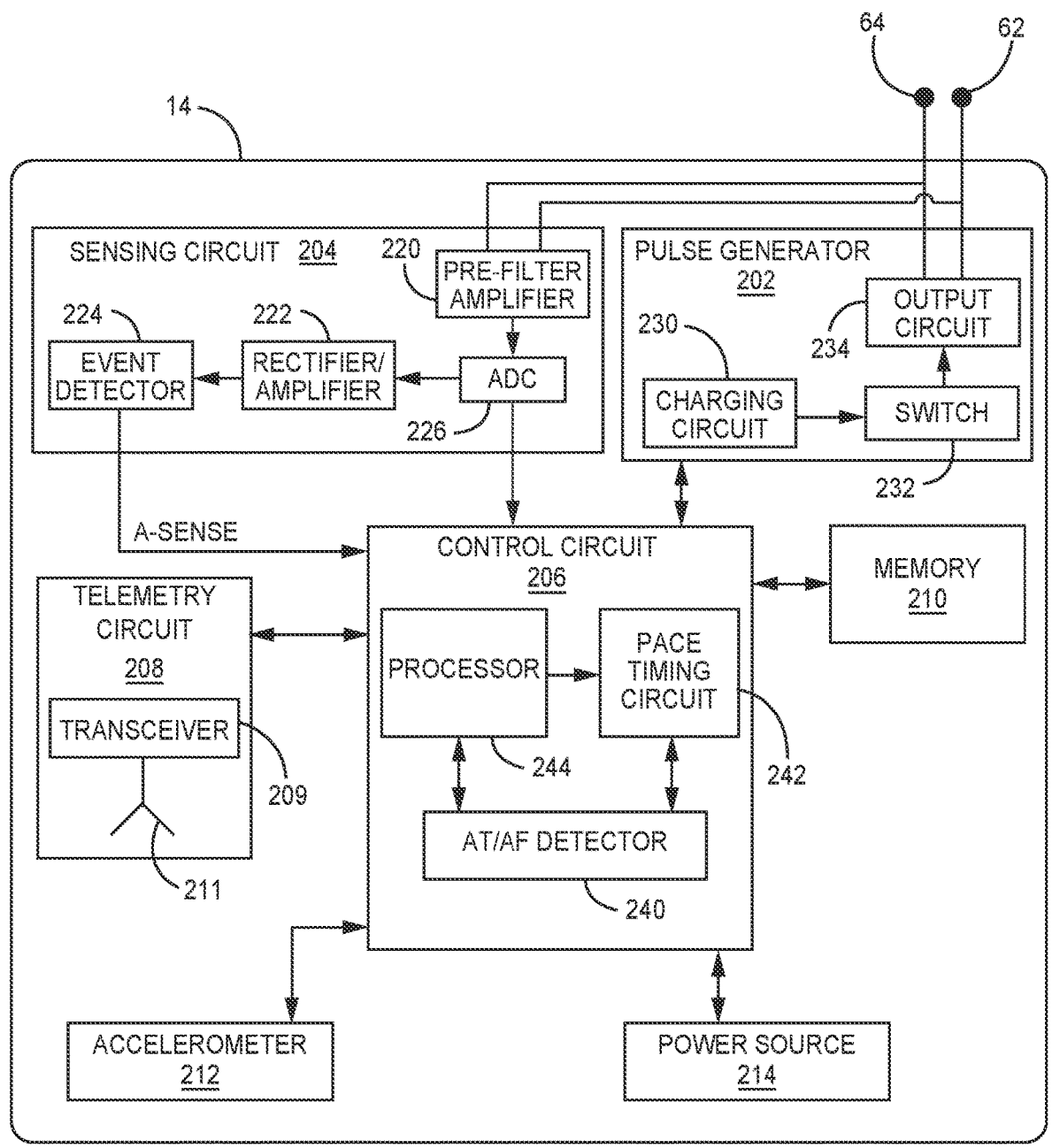
FIG. 4 is a conceptual diagram of an example configuration of the atrial pacemaker of FIG. 1 according to one example.

FIG. 4 is a conceptual diagram of an example configuration of pacemaker 14 configured to sense cardiac signals, detect AT/AF and deliver pacing therapy according to one example. Pacemaker 14 includes a pulse generator 202, a cardiac electrical signal sensing circuit 204, a control circuit 206, memory 210, telemetry circuit 208, an optional accelerometer 212, and a power source 214. The various circuits represented in FIG. 4 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive at least one cardiac electrical signal via electrodes coupled to pacemaker 14, e.g., electrodes 62 and 64 (and/or electrode 65 as shown in FIG. 2). The cardiac electrical signal, e.g., from electrodes 62 and 64 as shown in FIG. 3, may be received by a pre-filter and amplifier circuit 220. Pre-filter and amplifier circuit 220 may include a high pass filter to remove DC offset, e.g., a 2.5 to 5 Hz high pass filter, or a wideband filter having a bandpass of 2.5 Hz to 100 Hz or narrower to remove DC offset and high frequency noise. Pre-filter and amplifier circuit 220 may further include an amplifier to amplify the "raw" cardiac electrical signal passed to analog-to-digital converter (ADC) 226. ADC 226 may include a digital filter having a specified bandpass frequency range for improving the signal strength of the cardiac event signals of interest, e.g., P-waves, and attenuate other signals, such as 50 and 60 Hz noise. ADC 226 may pass a multi-bit, digital electrogram (EGM) signal to control circuit 206 for use by control circuit 206 in identifying cardiac electrical events (e.g., P-waves attendant to atrial depolarizations and FFRWs attendant to ventricular depolarizations), determining maximum peak amplitudes of sensed cardiac event signals, and/or performing morphology analysis for detecting various atrial arrhythmias. A narrow-band filtered, digital signal from ADC 226 may be passed to rectifier and amplifier circuit 222, which may include a rectifier and amplifier for passing the rectified atrial electrical signal to cardiac event detector 224.

Cardiac event detector 224 may include a sense amplifier, comparator or other detection circuitry that compares the incoming rectified, cardiac electrical signal to a cardiac event sensing threshold, which may be an auto-adjusting threshold. For example, when the incoming signal crosses a P-wave sensing threshold, the cardiac event detector 224 generates an atrial sensed event signal (A-sense) that is passed to control circuit 206. The atrial sensed event signal may correspond to a true intrinsic P-wave but may sometimes correspond to an FFRW falsely oversensed as a P-wave. In other examples, cardiac event detector 224 may receive the digital output of ADC 226 for sensing P-waves by a comparator, waveform morphology analysis of the digital EGM signal or other P-wave sensing techniques. Sensing circuit 204 may include multiple sensing channels for sensing atrial event signals, e.g., P-waves, and for sensing ventricular event signals, e.g., R-waves which may be FFRWs when the sensing electrodes are implanted in an atrial location. In some examples, sensing circuit 204 includes a P-wave sensing channel and an FFRW sensing channel. An example configuration of sensing circuit 204 is described below in conjunction with FIG. 5.

Processor 244 of control circuit 206 may provide sensing control signals to sensing circuit 204, e.g., P-wave sensing threshold control parameters such as sensitivity and various blanking and refractory intervals applied to the atrial electrical signal for controlling P-wave sensing. Atrial sensed event signals passed from cardiac event detector 224 to control circuit 206 may be used for scheduling atrial pacing pulses by pace timing circuit 242 and for determining atrial event intervals, also referred to herein as PP intervals or "PPIs," which may be used by control circuit 242 in detecting AT/AF.

Accelerometer 212 may include piezoelectric sensors or MEMS devices for sensing an atrial acceleration signal. Accelerometer 212 may be a single axis accelerometer or a multi-axis accelerometer, e.g., a two-dimensional or three-dimensional accelerometer, with each axis providing an axis signal that may be analyzed individually or in combination for sensing acceleration signals. Accelerometer 212 produces an electrical signal correlated to motion or vibration of accelerometer 212 (and pacemaker 14), e.g., when subjected to flowing blood, cardiac motion and patient body motion.

The accelerometer 212 may include one or more filter, amplifier, rectifier, analog-to-digital converter (ADC) and/or other components for producing an acceleration signal that may be passed to control circuit 206 for use in detecting ventricular and/or atrial mechanical event signals attendant to ventricular and atrial contractions, respectively. Control circuit 206 may additionally determine a patient physical activity metric for controlling rate response pacing from the acceleration signal received from accelerometer 212.

In various examples, the acceleration signal received from accelerometer 212 may be filtered by a high pass filter, e.g., a 10 Hz high pass filter, or a bandpass filter, e.g., a 10 Hz to 30 Hz bandpass filter. The filtered signal may be digitized by an ADC and optionally rectified for use by control circuit 240 for detecting atrial and/or ventricular mechanical event signals. A vector signal produced by an individual axis or combination of two or more axes of a multi-axis accelerometer may be filtered by a band pass or low pass filter, e.g., a 1-10 Hz bandpass filter or a 10 Hz low pass filter, digitized by an ADC and rectified for use by processor 244 of control circuit 206 for determining a patient physical activity metric. Various activity metrics may be derived from the accelerometer signal by control circuit 206 that are correlated to patient physical activity. For instance, the accelerometer-based activity metric derived from the accelerometer signal may be obtained by integrating the absolute value of a selected accelerometer vector signal over a predetermined time duration (such as 2 seconds). The selected accelerometer axis signal may be filtered by a 1-10 Hz bandpass filter, rectified and sampled at 128 Hz in one example. The amplitude of the sampled data points over a two-second interval may be summed to obtain the activity metric. This activity metric may be referred to as an "activity count" and is correlated to the acceleration due to patient body motion imparted on the pacemaker 14 during the predetermined time interval. The 2-second (or other time interval) activity counts may be used by control circuit 206 for determining a sensor indicated pacing rate (SIR) for use in controlling rate response pacing. In other examples, the activity count may be further processed, e.g., the 2-second interval activity counts may be averaged or summed over multiple intervals, to determine a patient physical activity metric for use in controlling rate response pacing. The techniques disclosed herein for detecting AT/AF are not required to be implemented in a pacemaker configured to provide rate response pacing based on patient physical activity metrics determined from an acceleration signal and do not require the pacemaker to include accelerometer 212 in some examples.

Control circuit 206 includes AT/AF detector circuit 240, pace timing circuit 242 and processor 244. Control circuit 206 may receive atrial sensed event signals and/or digital cardiac electrical signals from sensing circuit 204 for use in detecting and confirming P-waves and detecting AT/AF and controlling atrial pacing. For example, atrial sensed event signals may be passed to pace timing circuit 242 for starting an atrial pacing escape interval for use in controlling the timing of pacing pulses delivered by pulse generator 202. Processor 244 may include one or more clocks for generating clock signals that are used by pace timing circuit 242 to time out a pacing escape interval, e.g., a permanent lower rate pacing interval for treating bradycardia or a temporary lower rate interval for providing rate response pacing. The pacing escape interval may be restarted by pace timing circuit 242 in response to each atrial electrical event, e.g., upon receipt of each atrial sensed event signal from event detector 224 or upon delivery of each atrial pacing pulse by pulse generator 202.

When an atrial sensed event signal is received by control circuit 206 before the pacing escape interval expires, pace timing circuit 242 may pass the time elapsed of the pacing escape interval to processor 244 as the atrial event interval or PPI, between two consecutively received atrial sensed event signals (or between an atrial pacing pulse and a subsequently sensed atrial event signal). When an atrial sensed event signal is not received by control circuit 206 before expiration of the pacing escape interval, pulse generator 202 generates an atrial pacing pulse in response to the pacing escape interval expiration. The pacing escape interval may be adjusted according to a rate response pacing rate that is set by control circuit 206, e.g., based on the accelerometer signal.

When pacemaker 14 is configured for delivering ventricular pacing via the native ventricular conduction system, e.g., as described in conjunction with FIG. 2, control circuit 206 may set a ventricular pacing escape interval, which may be an atrioventricular (AV) pacing interval for controlling the timing of a ventricular pacing pulse delivered to His bundle, for example, to control an atrial synchronous ventricular pacing pulse. In other instances, the ventricular pacing interval may be a lower rate interval set for delivering pacing pulses to maintain a minimum ventricular rate or a temporary lower rate interval set according to a patient physical activity metric to provide rate responsive pacing.

Pulse generator 202 generates electrical pacing pulses upon expiration of a pacing escape interval set by pace timing circuit 242. The pacing pulses can be delivered to the patient's heart via cathode electrode 64 and return anode electrode 62. Processor 244 may retrieve programmable pacing control parameters from memory 210, such as pacing pulse amplitude and pacing pulse width, which are passed to pulse generator 202 for controlling pacing pulse delivery. Pulse generator 202 may include charging circuit 230, switching circuit 232 and an output circuit 234. Charging circuit 230 is configured to receive current from power source 214 and may include a holding capacitor that may be charged to a pacing pulse amplitude under the control of a voltage regulator included in charging circuit 230. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing escape interval and kept closed for a programmed pacing pulse width to enable discharging of the holding capacitor of charging circuit 230. The holding capacitor, previously charged to the pacing pulse voltage amplitude, is discharged across electrodes 62 and 64 (or other selected pacing electrode vector when available) through the output capacitor of output circuit 234 for the programmed pacing pulse duration.

AT/AF detector circuit 240 may receive PPIs from pace timing circuit 242 for detecting PPIs meeting AT/AF detection interval criteria. For example, an AT/AF detection interval may be defined which is compared to a PPI by AT/AF detector circuit 240. The AT/AF detection interval may be programmable between 150 to 450 milliseconds (ms) in various examples and may be nominally programmed to 300 ms, corresponding to an atrial rate of at least 200 beats per minute. When a PPI falls is less than or equal to the AT/AF detection interval, a counter may be increased to count the number of AT/AF intervals. In some examples a counter may be configured to count the number of PPIs determined to be an AT/AF interval out of a rolling, predetermined number of most recent PPIs. The counter may be configured as an X of Y counter for counting how many PPIs are less than or equal to the AT/AF detection interval out of the most recent PPIs. When at least X of Y AT/AF intervals are detected, an AT/AF episode may be suspected based on the PPIs. In an illustrative example, when at least 12 out of the most recent 16 PPIs are 300 ms or less, and FFRW oversensing criteria are not met as further described below, AT/AF onset criteria may be met. Control circuit 206 may switch from a non-AT/AF operating state, during which PPIs are monitored, to an AT/AF onset operation state during which control circuit 206 may determine if AT/AF detection criteria are met. The values of X and Y used for determining when the criterion of X out Y AT/AF intervals is met may be programmable between 1 to 24 (X values) out of 8 to 24 (Y values), as examples.

As disclosed herein, when AT/AF detection interval criteria (e.g., X of Y AT/AF intervals) are met, AT/AF detector circuit 244 may determine whether FFRW oversensing criteria are met, e.g., as described below in conjunction with FIG. 10. When AT/AF detection interval criteria are met and FFRW oversensing criteria are not met, AT/AF detector circuit 240 may determine that AT/AF onset criteria are met. As used herein, the term "AT/AF onset criteria," therefore, refers to criteria that require at least a predetermined number of atrial cycles (PPIs) that are less than or equal to a programmed AT/AF detection interval threshold as evidence of atrial tachyarrhythmia. Additionally, the AT/AF onset criteria may further require that FFRW oversensing criteria are not met. As used herein, the term "FFRW oversensing criteria" refers to interval criteria applied to PPIs and/or amplitude criteria applied to atrial sensed event peak amplitudes that identifies at least one sequence of at least two atrial cycles as an FFRW oversensing sequence because it includes at least one relatively long PPI and/or at least one relatively low peak amplitude. In one example, the FFRW oversensing criteria is defined to include interval criteria that requires at least one sequence of at least two consecutive atrial cycles having a long-short or a short-long PPI pattern or at least one PPI that is longer than the AT/AF detection interval threshold or a multiple thereof. Additionally or alternatively, the FFRW oversensing criteria may be defined to include amplitude criteria that requires that the peak amplitudes of the sensed atrial events of the at least one sequence of at least two atrial cycles include alternating relatively higher and lower peak amplitudes (e.g., high-low-high or low-high-low) and/or at least one of the atrial sensed event peak amplitudes being less than a predefined maximum FFRW threshold amplitude. Examples of FFRW oversensing criteria are described below, e.g., in conjunction with FIGS. 9 and 10.

In response to determining that AT/AF onset criteria are met, AT/AF detector circuit 240 may analyze the cardiac electrical signal, including PPIs received from pace timing circuit 242, to determine when AT/AF termination criteria are met. Various operating states of AT/AF detector circuit 240 are described below in conjunction with FIG. 7 for detecting AT/AF and detecting termination of AT/AF, even in the presence of FFRW oversensing.

Control circuit 206 may respond to an AT/AF detection by AT/AF detector circuit 240 by storing related data in memory 210. Stored data may include an episode of the cardiac electrical signal, representative of the detected AT/AF episode with a time and date stamp. Stored data may include an episode of the acceleration signal received from accelerometer 212. Since the acceleration signal may include atrial event signals corresponding to atrial contraction, the acceleration signal may be stored, with the atrial EGM signal in some cases, during an AT/AF episode. The acceleration signal and the EGM signal may be transmitted by telemetry circuit 208 to external device 20 or another implanted device, e.g., ICD 112 as shown in FIG. 3A. Other stored data may include the AT/AF episode duration, maximum or average rate, total AT/AF burden (e.g., over a 24 hour period) or other AT/AF episode related data.

Additionally or alternatively, control circuit 206 may respond to the AT/AF detection by transmitting a signal via telemetry circuit 208 indicating that AT/AF is detected. Another medical device, e.g., ICD 112 of FIG. 3A, may respond to the transmitted signal by delivering a therapy to terminate the AT/AF or by withholding a VT/VF detection or a VT/VF therapy, as examples. In still other examples, control circuit 206 may respond to an AT/AF detection by controlling pulse generator 202 to deliver ATP therapy in some examples to overdrive pace the atria in an attempt to terminate the AT/AF. When pacemaker 14 is positioned for delivering pacing pulses for capturing the His bundle from an atrial implant location, e.g., as shown in FIG. 2, control circuit 206 may control pulse generator 202 to deliver non-atrial tracking ventricular pacing pulses via the native ventricular conduction system in response to detecting AT/AF. When pacemaker 14 is operating in an atrial synchronous ventricular pacing mode, by sensing atrial P-waves and delivering ventricular pacing pulses via the His-Purkinje system from an atrial approach, control circuit 206 may switch the pacing mode from an atrial synchronous pacing mode to an atrial asynchronous or non-atrial tracking ventricular pacing mode.

In yet another example, in response to detecting AT/AF control circuit 206 may disable rate response pacing based on a signal from accelerometer 212. During AT/AF, the acceleration signal produced by accelerometer 212 may include a high frequency of oscillations contributing to activity counts, potentially resulting in an artificially high SIR. Accordingly, in some examples, an AT/AF detection is responded to by control circuit 206 by disabling acceleration-based rate response pacing.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Memory 210 may store AT/AF intervals determined from the atrial electrical signal for use by control circuit 206 in detecting AT/AF and other data related to AT/AF episode detections, such as the duration of a detected AT/AF episode, the median or mean rate of the episode, the atrial EGM signal recorded during the detected episode, the accelerometer signal recorded during the detected episode, and the date and time of the detected episode. Memory 210 may store other data determined from sensed signals and related to therapy delivery. Memory 210 may also store programmable control parameters and instructions executed by control circuit 206 for detecting AT/AF, controlling atrial (and/or ventricular) pacing and other pacemaker functions.

Telemetry circuit 208 may include a transceiver 209 and antenna 211 for transmitting and receiving data, e.g., via a radio frequency (RF) communication link. Telemetry circuit 208 may be capable of bi-directional communication with external device 20 (FIG. 1) as described above. Cardiac electrical signals, and/or data derived therefrom, may be transmitted by telemetry circuit 208 to external device 20. Programmable control parameters and algorithms for sensing cardiac event signals, detecting AT/AF and controlling pacing therapies delivered by pulse generator 202 may be received by telemetry circuit 208 and stored in memory 210 for access by control circuit 206. AT/AF detection signals may be transmitted by telemetry circuit 208 for receipt by another medical device, e.g., ICD 112 shown in FIG. 3A.

Power source 214 provides power to each of the other circuits and components of pacemaker 14 as required. Power source 214 may include one or more energy storage devices, such as one or more rechargeable or non-rechargeable batteries. The connections between power source 214 and other pacemaker circuits and components are not explicitly shown in FIG. 4 for the sake of clarity but are to be understood from the general block diagram of FIG. 4. For example, power source 214 may provide power as needed to charging and switching circuitry included in pulse generator 202; amplifiers, ADC 226 and other components of sensing circuit 204; telemetry circuit 208; memory 210 and accelerometer 212.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, algorithms for detecting AT/AF may be implemented in control circuit 206 executing instructions stored in memory 210. Providing software, hardware, and/or firmware to accomplish the described functionality in the context of any modern medical device, given the disclosure herein, is within the abilities of one of skill in the art.

Figure 5:
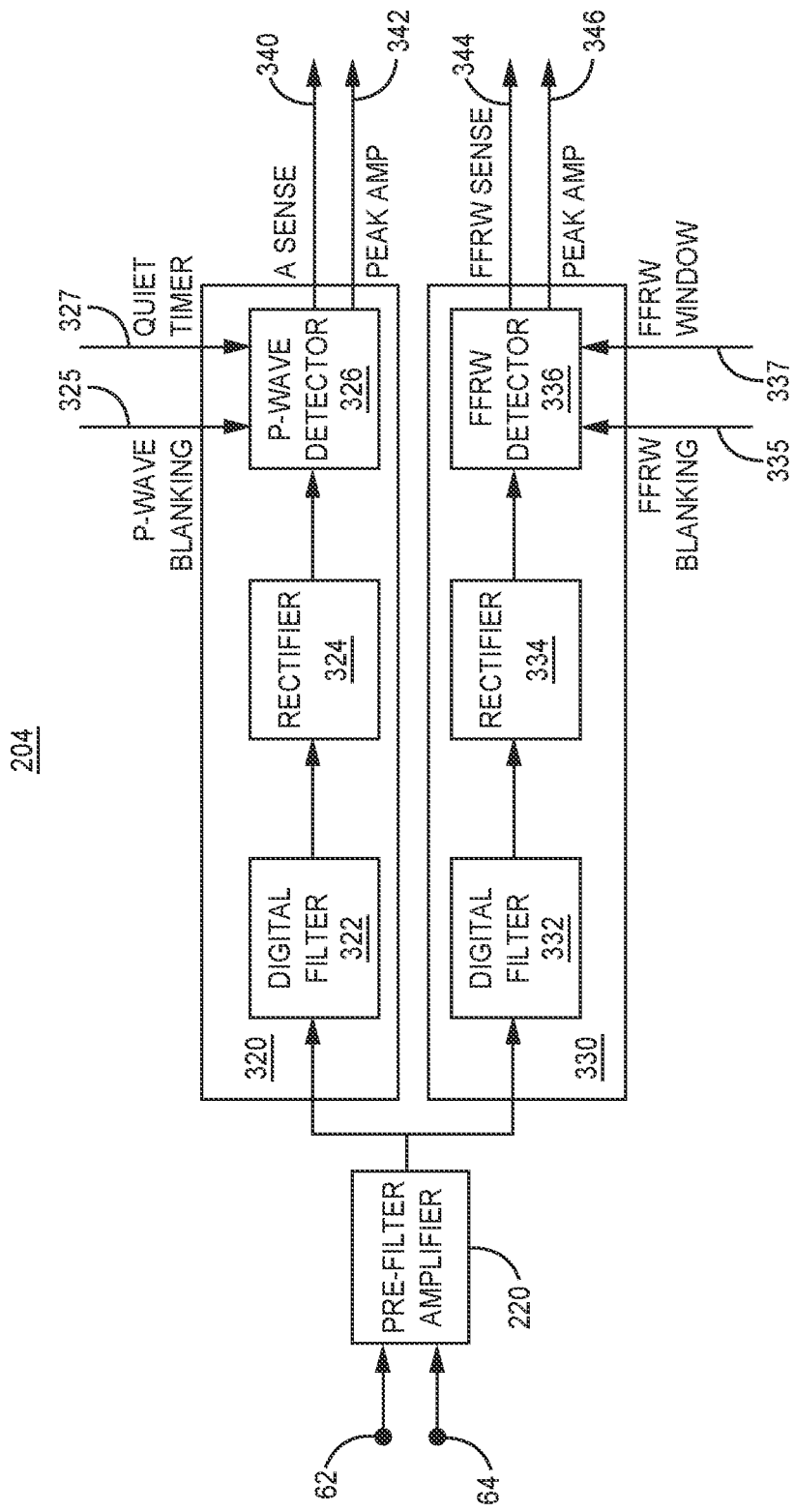
FIG. 5 is a conceptual diagram of a P-wave sensing channel and an FFRW sensing channel that may be included the atrial pacemaker of FIG. 4 according to some examples.

FIG. 5 is a conceptual diagram of a P-wave sensing channel 320 and an FFRW sensing channel 330 that may be included in sensing circuit 204 in some examples. As described above, sensing circuit 204 may include an input filter, shown as pre-filter/amplifier 220, shown coupled to electrodes 62 and 64 for receiving the cardiac electrical signal sensed from an atrial location of electrodes 62 and 64. The pre-filter/amplifier 220 may be shared between P-wave sensing channel 320 and FFRW sensing channel 330. In other examples, separate input filters, each receiving the cardiac electrical signal via electrodes 62 and 64 (and/or other electrodes if available such as electrode 65 shown in FIG. 2), may be included in each of P-wave sensing channel 320 and FFRW sensing channel 330.

P-wave sensing channel 320 may include a digital filter 322, rectifier 324, and P-wave detector 326. FFRW sensing channel 330 is optional in some examples. When included, FFRW sensing channel 330 may include a digital filter 332, rectifier 334 and FFRW detector 336. In other examples, P-wave sensing channel 320 and FFRW sensing channel 330 may share some components such as a digital filter and rectifier with the output provided separately to each of the P-wave detector 326 and FFRW detector 336.

In the example shown, the digital filter 322 of the P-wave sensing channel 320 and the digital filter 334 of the FFRW sensing channel 330 may have different bandpass frequency ranges in order to enhance the P-wave signal strength and attenuate the FFRW signal in the P-wave sensing channel 320 to minimize the likelihood of oversensing FFRWs. The digital filter 334 of FFRW sensing channel 330 may have a bandpass frequency range that minimizes attenuation of the FFRW to enable positive detection of the FFRW. In one example, P-wave sensing channel digital filter 322 may be a 20 to 60 Hz bandpass filter providing a filtered, digital signal to rectifier 324. The FFRW sensing channel digital filter 332 may have lower cutoff frequencies, e.g., a 6.5 to 55 Hz bandpass frequency range, for providing a filtered, digital signal to rectifier 334.

P-wave detector 326 may receive timing control signals including a P-wave blanking signal 325 for controlling a blanking period applied to the P-wave detector 326 following a previously sensed atrial event or an atrial pacing pulse delivered by pulse generator 202. P-wave detector 326 may receive a quiet timer signal 327 that sets a quiet time interval when the P-wave detector 326 determines that the rectified signal input received by P-wave detector 326 crosses the P-wave sensing threshold. When the quiet time is active, the P-wave detector 326 does not sense an atrial event even if another P-wave sensing threshold crossing occurs. In this manner, quiet timer signal 327 avoids sensing the same P-wave multiple times or repetitively sensing of high frequency noise. In one example, the quiet timer signal 327 may activate a quiet time for at least 10 ms and up to 40 ms, as examples, in response to a P-wave sensing threshold crossing. In another examples, quite timer signal 327 may activate a quiet time of 30 ms. In some instances, quiet timer signal 327 may operate in retrigger mode, which restarts the quiet time interval if another P-wave sensing threshold crossing occurs during the quiet time interval. If the re-triggered quiet timer is still active (e.g., retriggered by a threshold crossing without timing out) when an atrial pacing interval expires, a pacing pulse will be delivered. In this way, high frequency noise in the atrial electrical signal that may cause frequent P-wave sensing threshold crossings, and false atrial sensed event signals, does not cause pacing inhibition.

The operation of P-wave detector 326 in applying a P-wave sensing threshold to the rectified atrial electrical signal is described below in conjunction with FIG. 6. When the filtered, rectified signal received by P-wave detector 326 crosses a P-wave sensing threshold amplitude outside a blanking period (when the quiet timer is not active), P-wave detector 326 generates an atrial sensed event signal 340. Atrial sensed event signal 340 is passed to control circuit 206 for use by pace timing circuit 242 in scheduling atrial pacing pulses and determining atrial event intervals or PPIs (although some atrial sensed event signals may not correspond to true P-waves, e.g., when an FFRW or noise is oversensed). As used herein, the term "atrial event" refers to an atrial electrical event that starts or ends an atrial event interval or atrial cycle. The atrial event may be a pacing pulse generated by pulse generator 202 or an intrinsic P-wave sensed by P-wave sensing channel 320. The time interval between two consecutive atrial events, which may be two pacing pulses, two atrial sensed event signals, or one pacing pulse and one atrial sensed event signal may be determined as a PPI, which represents one atrial cycle. In some instances, an FFRW or electrical signal noise may be oversensed resulting in a false atrial sensed event signal and false PPI. The PPIs are used by AT/AF detector circuit 240 for detecting AT/AF and the termination of AT/AF as described below. According to the techniques disclosed herein, an AT/AF episode and termination of the AT/AF episode may be detected by control circuit 206, even in the presence of FFRW oversensing, based on analysis of PPIs and peak amplitudes of the atrial electrical signal.

In some examples, P-wave detector 326 includes a peak detector for determining the maximum peak amplitude of the atrial electrical signal following the P-wave sensing threshold crossing. P-wave detector 326 may provide a maximum peak amplitude signal 342 to control circuit 202. As described below, the maximum peak amplitude signal 342 may be used by AT/AF detector circuit 240 for use in classifying a sequence of at least two atrial cycles as a non-FFRW oversensing sequence or as an FFRW oversensing sequence in some examples. By classifying FFRW oversensing sequences as non-AT/AF sequences, AT/AF detector circuit 240 may be configured to reliably detect AT/AF, avoiding false AT/AF detections in the presence of FFRW oversensing, and detect termination of an AT/AF episode in the presence of FFRW oversensing.

When FFRW sensing channel 330 is included, the FFRW detector 336 receives the rectified signal input from rectifier 334. In response to the signal crossing an FFRW sensing threshold amplitude during an FFRW window, FFRW detector 336 may generate an FFRW sensed event signal 344. FFRW detector 336 may receive an FFRW blanking signal 335 applied following an atrial sensed event signal 340 or an atrial pacing pulse generated by pulse generator 202. FFRW detector 336 may receive an FFRW window signal 337 for setting the duration of a sensing window after the FFRW blanking period 335, during which an FFRW sensing threshold amplitude crossing causes FFRW detector 336 to generate an FFRW sense event signal 344.

FFRW detector 336 may include a peak detector for determining the maximum peak amplitude of the atrial electrical signal following an FFRW sensing threshold crossing. A maximum peak amplitude signal 346 indicating the peak amplitude associated with an immediately preceding FFRW sensed event signal 344 may be passed to control circuit 206. The maximum peak amplitude signal 346 may be used instead of or in addition to the peak amplitude signal 342 from the P-wave sensing channel 320 for use by AT/AF detector in classifying consecutive atrial cycles as FFRW sequences or non-FFRW sequences as described below.

Figure 6:
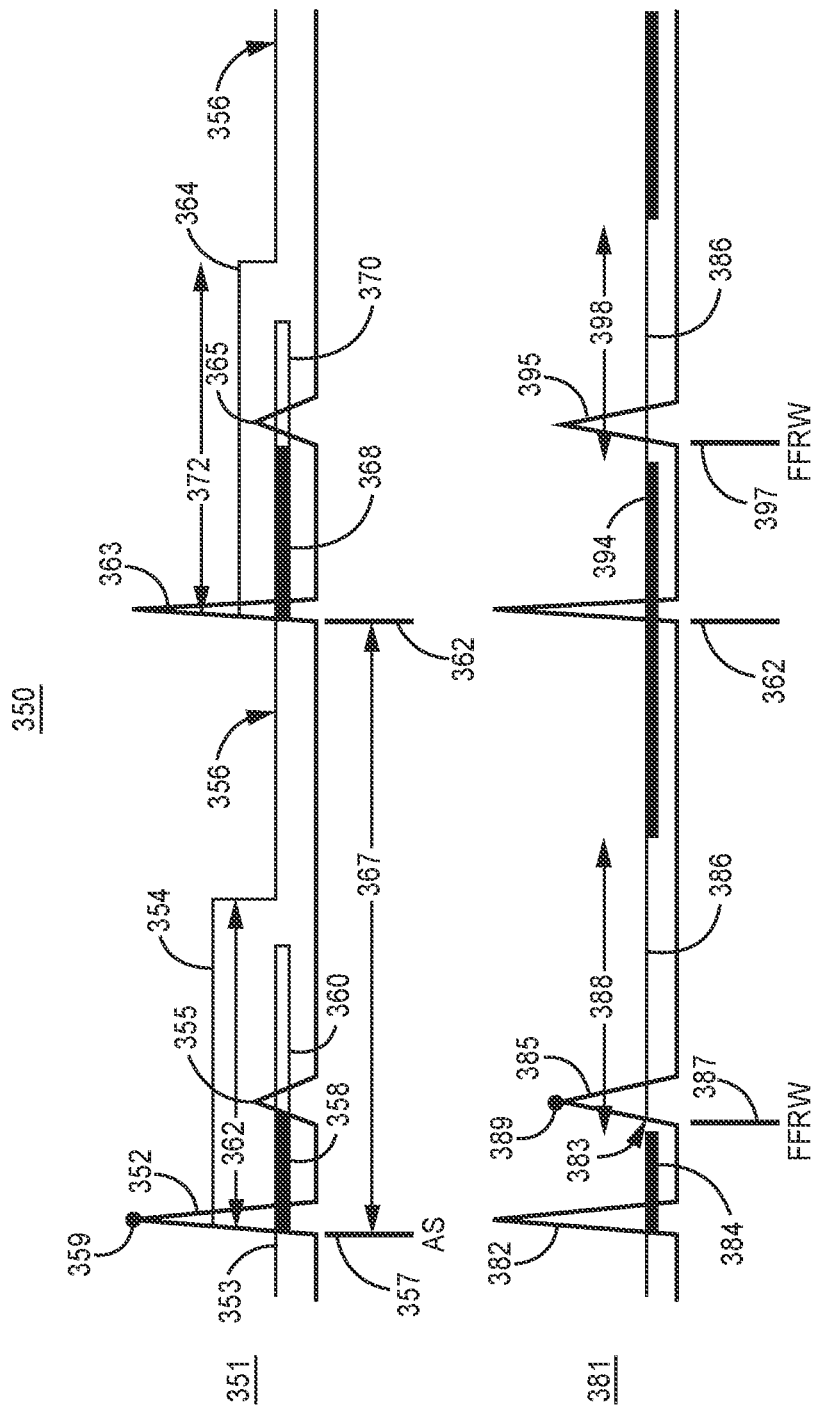
FIG. 6 is a diagram of P-wave sensing and FFRW sensing operations that may be performed by the sensing circuit of FIG. 5 according to some examples.

FIG. 6 is a diagram 350 of P-wave sensing and FFRW sensing operations that may be performed by sensing circuit 204 according to some examples. The top cardiac electrical signal 351 is a conceptual representation of the atrial electrical signal that is filtered and rectified by P-wave sensing channel 320 and passed to P-wave detector 326 (shown in FIG. 5). Signal 351 includes an intrinsic P-wave 352 and subsequent FFRW 355 followed by an atrial pacing pulse 362 and subsequent pacing-evoked P-wave 363 and FFRW 365. In response to a P-wave sensing threshold crossing 353, P-wave detector 326 generates an atrial sensed event signal 357 and starts a post-sense blanking period 358 and a post-sense refractory period 360. In some examples, P-wave detector 326 may determine a maximum peak amplitude 359 following the sensing threshold crossing 353, e.g., within blanking period 358, as the atrial sensed event peak amplitude. This peak amplitude 359 may be used by the P-wave sensing channel in setting the starting P-wave sensing threshold amplitude 354. For example, P-wave detector 326 may set the starting P-wave sensing threshold amplitude 354 to a percentage of maximum peak amplitude 359, which may be between 50% and 70%, as examples. In some examples, the peak amplitude 359 is used by control circuit 206 for identifying alternating high and low peak amplitudes that may correspond to FFRW oversensing.

Upon expiration of the post-sense blanking period 358, which may be set to 50 to 250 ms as examples, P-wave detector 326 applies the starting P-wave sensing threshold 354 to atrial electrical signal 351. If the atrial electrical signal 351 crosses the P-wave sensing threshold amplitude 354 during the refractory period 360, P-wave detector 326 may generate a refractory sense signal (not shown in the example of FIG. 6). The refractory period 360 may extend 150 to 300 ms from the atrial sensed event signal 357. A refractory sense signal generated by P-wave detector 326 may be used by control circuit 206 in determining PPIs for detecting AT/AF but may be ignored for purposes of scheduling pacing pulses in some examples. Pace timing circuit 242 may start an atrial pacing interval 367 upon receiving atrial sensed event signal 357 to schedule the atrial pacing pulse 362. Atrial pacing pulse 362 is delivered upon expiration of the pacing interval 367 when a non-refractory atrial sensed event signal is not generated during the pacing interval 367.

In the example shown, P-wave detector 326 (shown in FIG. 5) holds the first P-wave sensing threshold amplitude 354 for a drop time interval 362 starting from the atrial sensed event signal 357. Upon expiration of the drop time interval 362 (without a P-wave sensing threshold amplitude crossing), P-wave detector 326 decreases the P-wave sensing threshold to a second, lower sensing threshold amplitude 356. The adjustment from the starting, higher sensing threshold amplitude 354 to the second lower sensing threshold amplitude 356 may be made in one or more step decrements or decreased according to a decay rate. The drop time interval 362 may be set to include the expected timing of the FFRW 355 to reduce the likelihood of oversensing the FFRW by P-wave detector 326. The lower P-wave sensing threshold amplitude 356 may correspond to a programmed sensitivity for P-wave sensing, e.g., 0.1 to 0.3 mV. The programmed sensitivity, sometimes referred to as the "sensing floor," is the minimum P-wave sensing threshold amplitude applied by P-wave detector 326 to the atrial electrical signal for sensing P-waves. In the example shown, the atrial electrical signal 351 does not cross the lower P-wave sensing threshold amplitude 356 prior to expiration of pacing interval 367, resulting in a pacing pulse 362 being delivered by pulse generator 202.

P-wave detector 326 starts a post-pace blanking period 368 and post-pace refractory period 370 in response to the pacing pulse 362. P-wave detector 326 may set the P-wave sensing threshold to a post-pace starting threshold amplitude 364, held for a drop time interval 372, then reduce the P-wave sensing threshold to the second, lower sensing threshold amplitude 356, which may be equal to the programmed sensitivity for sensing P-waves. The post-pace blanking period 368, the post-pace refractory period 370, and the post-pace drop time interval 372 may be set equal to or different than the post-sense blanking period 358, post-sense refractory period 360 and post-sense drop time interval 362, respectively. For example, the post-pace blanking period 368, post-pace refractory period 370 and post-pace drop time interval 372 may be relatively longer than the analogous post-sense time intervals to account for pacing artifact duration and/or a time delay from the pacing pulse 362 to the subsequent atrial and ventricular depolarizations associated with the pacing-evoked P-wave 363 and the subsequent FFRW 365.

The lower atrial electrical signal 381 is a conceptual representation of the filtered and rectified signal passed to FFRW detector 326 in FFRW sensing channel 330. The atrial electrical signal 381 includes a P-wave 382 (corresponding to P-wave 352 in the top signal 351) and an FFRW 385 (corresponding to FFRW 355 of the top signal 351). The FFRW 385 in atrial electrical signal 381 may be less attenuated than the FFRW 355 in the top signal 351 due to the different filtering bandpass frequency ranges of the FFRW sensing channel 330 and the P-wave sensing channel 320. The different filtering bandpass frequency ranges are used in order to increase the likelihood of sensing the FFRW 385 by FFRW detector 336 (shown in FIG. 5) and decrease the likelihood of oversensing the FFRW 355 by P-wave detector 326.

FFRW detector 336 may set an FFRW blanking period 384 in response to an atrial sensed event signal 357 generated by P-wave sensing channel 320. FFRW detector 336 may set an FFRW sensing window 388 in response to the atrial sensed event signal 357. FFRW sensing window 388 may extend from the expiration of the FFRW blanking period 384 for a predetermined time interval that is expected to encompass an FFRW 385. For example, FFRW sensing window 388 may start approximately 50 to 200 ms after the atrial sensed event signal 357 and have a duration of 150 to 300 ms, as examples. FFRW detector 336 sets an FFRW sensing threshold amplitude 386, which may be a fixed or programmable threshold amplitude and may remain constant during the FFRW sensing window 388 in some examples. The FFRW sensing threshold amplitude 386 may be set to be greater than the baseline noise of atrial electrical signal 381 and may be less than or equal to (or in some cases greater than) the programmed P-wave sensitivity 356.

In response to the atrial electrical signal 381 crossing the FFRW sensing threshold amplitude 386 (at 383) during the sensing window 388, FFRW detector 336 may generate a sensed FFRW signal 387. In some examples, FFRW detector 336 determines the maximum peak amplitude 389 following the sensed FFRW signal 387, within sensing window 388, as the FFRW peak amplitude 389. The sensed FFRW signal 387 and/or the peak amplitude 389 may be passed to control circuit 206 and may be used in classifying a sequence of atrial cycles as an FFRW oversensing sequence as described below.

In response to a delivered atrial pacing pulse 362, FFRW detector 330 may set a post-pace blanking period 394 and a post-pace FFRW sensing window 398. The post-pace blanking period 394 and post-pace FFRW sensing window 398 may be set equal to or different than the post-sense FFRW blanking period 384 and post-sense FFRW sensing window 388, respectively. For example, an FFRW 395 may be expected to be later after an atrial pacing pulse 362 than the FFRW 385 following an atrial sensed event signal 357 associated with sensing an intrinsic P-wave. As such, the post-pace blanking period 394 may be longer than the post-sense blanking period 384. The post-pace sensing window 398 may extend later following pacing pulse 362 than the post-sense FFRW sensing window 388 extends following the atrial sensed event signal 357.

In response to the atrial electrical signal 381 crossing the FFRW sensing threshold amplitude 386 during the post-pace sensing window 398, FFRW detector 330 may generate a sensed FFRW signal 397 and determine a maximum peak amplitude of the atrial electrical signal 381 during the FFRW sensing window 398. In some examples, control circuit 206 may use the FFRW sensed event signal 394 and the peak amplitude for classifying sequences of atrial cycles as FFRW oversensing or non-FFRW oversensing sequences.

Figure 7:
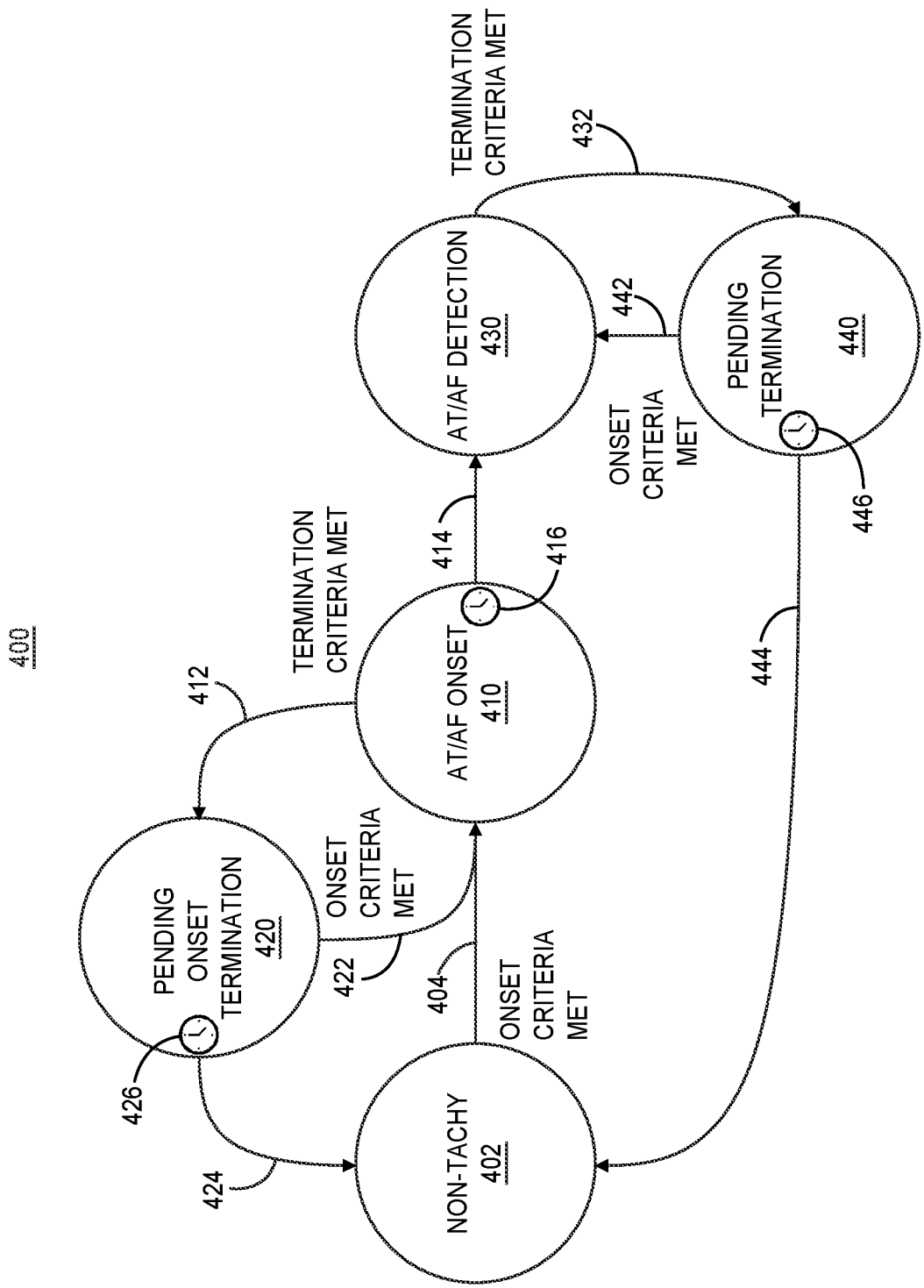
FIG. 7 is a conceptual diagram of operating states of a control circuit of the atrial pacemaker of FIG. 4 for detecting an AT/AF episode and detecting termination of the AT/AF episode according to some examples.

FIG. 7 is a diagram 400 of operating states of control circuit 206 for detecting AT/AF according to one example. The AT/AF detector circuit 240 of control circuit 206 may be configured to transition between operating in one of a non-tachyarrhythmia state 402, an AT/AF onset state 410, a pending onset termination state 420, an AT/AF detection state 430 and a pending termination state 440. The transitions between the different operating states (as indicated by arrows 404, 412, 414, 422, 424, 432, 442 and 444) occur in various instances in response to a determination by control circuit 206 that AT/AF onset criteria are met, a determination by control circuit 206 that termination criteria are met, or expiration of a timer.

For example, while operating in the non-tachyarrhythmia state 402, control circuit 206 may determine when AT/AF onset criteria are met by the cardiac electrical signal. In response to AT/AF onset criteria being met, control circuit 206 transitions (arrow 404) to the AT/AF onset state 410 and starts a detection timer 416 and may start an AT/AF duration timer (not shown in FIG. 7). During the AT/AF onset state 410, control circuit 206 switches from determining when AT/AF onset criteria are met to operating to determine if termination criteria are met by the sensed cardiac electrical signal. If termination criteria are met before the detection timer 416 expires, control circuit 206 transitions (arrow 412) to the pending onset termination state 420 and starts an onset termination timer 426. In the pending onset termination state 420, control circuit 206 switches back to operating to determine if onset criteria are met again by the cardiac electrical signal before the onset termination timer 426 expires. The onset termination timer 426 may be set to 0 to 120 seconds or between 0 and 60 seconds, as examples, and is set to 10 seconds in one example. If the onset termination timer 426 expires during the pending onset termination state 410 without onset criteria being met, control circuit 206 transitions (arrow 424) back to the non-tachyarrhythmia state 402 and clears the detection timer 416 (and the AT/AF duration timer if started). Control circuit 206 does not detect an AT/AF episode when the transition 424 is made from the pending onset termination state 420 back to the non-tachyarrhythmia state 402.

If, however, control circuit 206 determines during the pending onset termination state 420 that onset criteria are met again before the onset termination timer 426 expires, control circuit 206 transitions back to the AT/AF onset state 410 (arrow 422) and clears the onset termination timer 426. The detection timer 416 started earlier upon transitioning to the AT/AF onset state 410 from the non-tachyarrhythmia state 402 may continue to run while control circuit 206 operates in the pending onset termination state 420. If the detection timer 416 expires, control circuit 206 transitions (arrow 414) to the AT/AF detection state 430. The control circuit 206 detects an AT/AF episode after onset criteria are met and the termination criteria remain unmet for at least the duration of the detection timer 416. The detection timer may be set to 1 to 60 minutes in various examples and is set to 6 minutes in one example. If an AT/AF duration timer was started upon entering the AT/AF onset state 410, the AT/AF duration timer may continue to run upon transitioning to the AT/AF detection state 430. In other examples, the AT/AF duration timer may be started upon entering the AT/AF detection state 430. When control circuit 206 starts the AT/AF duration timer upon entering the AT/AF detection state, control circuit 206 may add the value of the AT/AF detection timer, e.g., 6 minutes, to a final value of the AT/AF duration timer (e.g., when termination is detected) to determine a total AT/AF episode duration.

Upon transitioning to or during the AT/AF detection state 430, control circuit 206 may generate one or more outputs to memory 210 in response to the AT/AF detection. For example, control circuit 206 may generate an AT/AF detection marker and a date and time stamp indicating detection of the AT/AF episode. An AT/AF detection signal may be transmitted by telemetry circuit 208 in response to the stored AT/AF detection marker. During the AT/AF onset state and/or during the AT/AF detection state 430, control circuit 206 may buffer a segment of the atrial EGM signal and/or the accelerometer signal in memory 210 as a representation of the atrial electrical signal and acceleration signal during the AT/AF episode. Control circuit 206 may generate various control signals for adjusting a pacing therapy generated by pulse generator 202. For example, rate response pacing based on the acceleration signal from accelerometer 212 may be disabled upon entering the AT/AF onset state 410 or upon entering the AT/AF detection state 430. In another example, control circuit 206 may generate control signals for causing pulse generator 202 to deliver an ATP therapy upon entering the AT/AF detection state 430.

In still other examples, control circuit 206 may generate control signals for causing pulse generator 202 to deliver pacing pulses to or in the area of the His bundle via tip electrode 64 for providing non-atrial tracking ventricular pacing via the native ventricular conduction system upon entering the AT/AF detection state 430. Ventricular pacing in an atrial asynchronous pacing mode may be started in response to entering the AT/AF onset state 410 or the AT/AF detection state 430. In other instances, when pacemaker 14 is delivering ventricular pacing pulses to or in the area of the His bundle in an atrial synchronous ventricular pacing mode, control circuit 206 may switch the pacing mode to an atrial asynchronous (non-atrial tracking) ventricular pacing mode.

In the AT/AF detection state 430, control circuit 206 operates to determine if termination criteria are met by the cardiac electrical signal. When the termination criteria are met, control circuit 206 transitions to the pending termination state 440 (arrow 432) and starts a termination timer 446. The termination timer 446 may be set to 0 to 120 seconds, as examples, and may be set to 20 seconds in some examples. The AT/AF duration timer (not illustrated in FIG. 7) that may be started upon entering the AT/AF onset state 410 may continue to run upon transitioning to the pending termination state 440. In the pending termination state 440, control circuit 206 determines if the onset criteria are met again before the termination timer 446 expires. When the onset criteria are met during the pending termination state 440, control circuit 206 returns to the AT/AF detection state 430 (arrow 442) and is still detecting the AT/AF episode (with the AT/AF duration timer still running). When the termination timer 446 expires without the onset criteria being met during the pending termination state 440, control circuit 206 transitions to the non-tachyarrhythmia state 402 (arrow 444). Termination of the AT/AF episode is detected by control circuit 206.

Upon transition 444 back to the non-tachyarrhythmia state 402, control circuit 206 may produce one or more outputs for storage in memory 210, which may include data related to the detected episode and/or control signals subsequently used by control circuit 206 and/or another pacemaker component, e.g., telemetry circuit 208 and/or pulse generator 202, for responding to the AT/AF termination according to any of the examples provided herein. For example, the total duration of the detected AT/AF episode may be stored based on the value of the AT/AF duration timer and/or other related episode data such as the maximum, mean or and/or minimum atrial rate (or corresponding PPIs). A signal indicating that AT/AF is no longer being detected may be transmitted by telemetry circuit 208. If accelerometer-based rate response pacing was disabled upon entering the AT/AF onset state 410 or the AT/AF detection state 430, control circuit 206 may re-enable accelerometer based rate response pacing. When non-atrial tracking ventricular pacing via the His-Purkinje system was started in response to entering the AT/AF onset state 410 or the AT/AF detection state 430, control circuit 206 may switch to a non-ventricular pacing mode (when AV conduction is intact) or switch to an atrial synchronous ventricular pacing mode.

Figure 8:
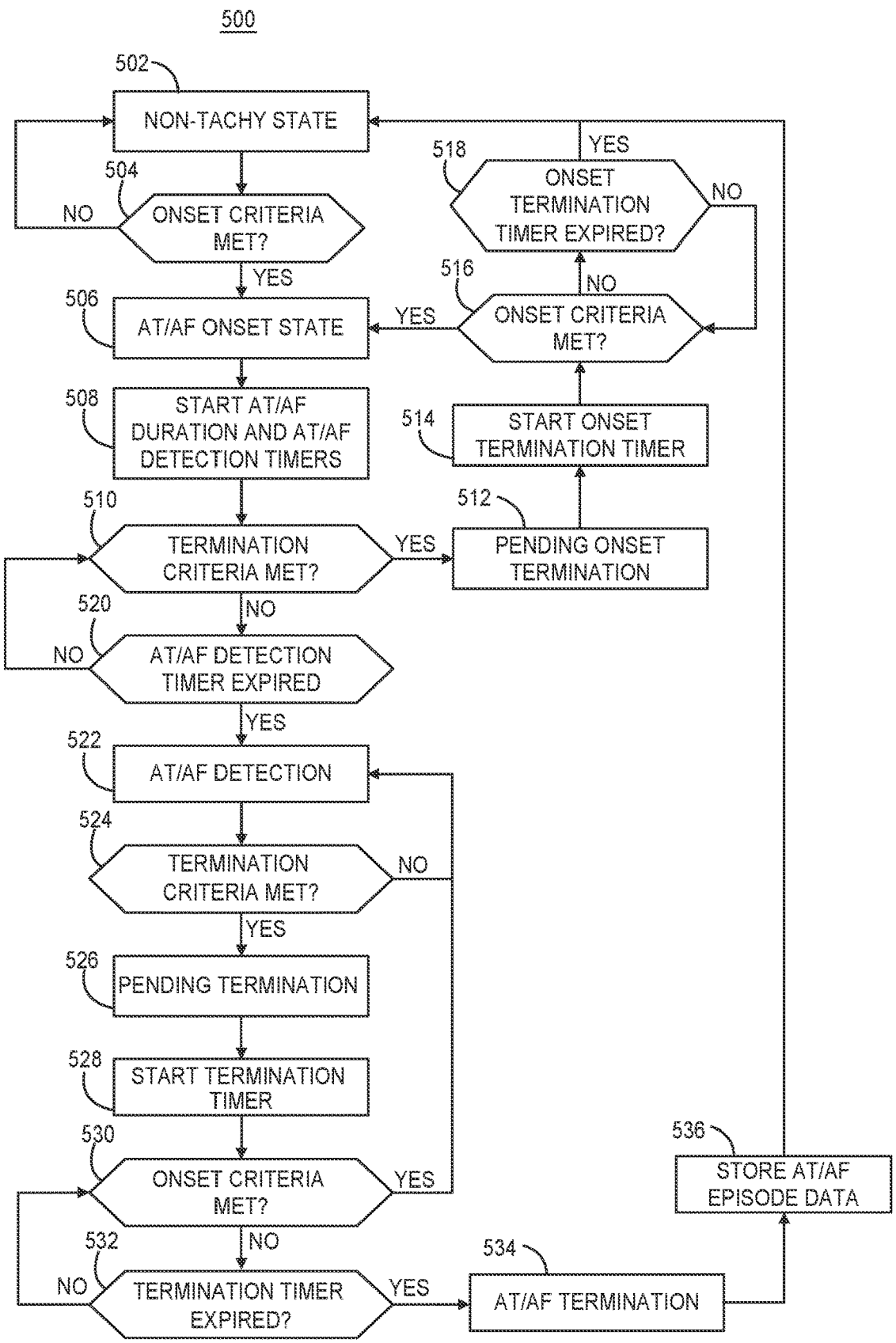
FIG. 8 is a flow chart of one example method for detecting AT/AF and detecting termination of AT/AF according to the operating states shown in FIG. 7.

FIG. 8 is a flow chart 500 of a method for detecting AT/AF and detecting termination of AT/AF according to the operating states shown in FIG. 7. With continued reference to both FIG. 7 and FIG. 8, control circuit 206 operates in the non-tachyarrhythmia state 402 at block 502 when AT/AF is not being detected. Control circuit 206 may remain in the non-tachyarrhythmia state 402 when determining PPIs that are greater than the AT/AF detection interval and/or pulse generator 202 is delivering atrial pacing pulses at a lower rate pacing interval or rate response pacing interval (e.g., in the absence of non-refractory atrial sensed event signals from sensing circuit 205). During the non-tachyarrhythmia operating state 402, control circuit 206 determines if the atrial electrical signal meets AT/AF onset criteria (also referred to herein as "onset criteria") at block 504. One method for determining when onset criteria are met is described below in conjunction with FIG. 9. The onset criteria may include interval criteria relating to PPIs meeting AT/AF detection interval criteria and not meeting FFRW oversensing interval criteria in some examples. The onset criteria may further include amplitude criteria, e.g., relating to alternating amplitudes that might satisfy FFRW oversensing amplitude criteria, which may prevent the onset criteria from being satisfied during the non-tachyarrhythmia operating state 402.

When onset criteria are met at block 504 during the non-tachyarrhythmia state, control circuit 206 transitions (arrow 404 in FIG. 7) to the AT/AF onset state at block 506. At block 508, control circuit 206 may start an AT/AF duration timer and an AT/AF detection timer (shown as timer 416 in FIG. 7) upon transitioning to the AT/AF onset state from the non-tachyarrhythmia state. Control circuit 206 determines if the cardiac electrical signal meets termination criteria during the AT/AF onset state at block 510 before the AT/AF detection timer expires at block 520. For example, control circuit 206 may analyze PPIs, maximum peak amplitudes, and/or frequency of atrial pacing for determining when termination criteria are met. An example method for determining that termination criteria are met is described below in conjunction with FIG. 11. When control circuit 206 determines that the termination criteria are met ("yes" branch of block 510) before the detection timer 416 expires (block 520), control circuit 206 transitions to the pending onset termination state at block 512, as indicated by transition arrow 412 in FIG. 7. Control circuit 206 does not detect AT/AF when the termination criteria are met before the detection timer 416 expires. A non-sustained AT/AF episode may have occurred or noise or FFRW oversensing may have caused the onset criteria to be met at block 504 due to false PPIs, for example.

Upon transitioning to the pending onset termination state (block 512), control circuit 206 starts the onset termination timer at block 514 and resumes analysis of the cardiac electrical signal for determining if the onset criteria are met again at block 516 before the onset termination timer expires at block 518. Any AT/AF interval counts or other cardiac electrical signal data that are buffered in memory 210 at the time that the termination criteria were met at block 510 may remain stored in memory 210 and used by control circuit 206 in determining if the onset criteria become satisfied again at block 516 before the onset termination timer expires (block 518). The onset termination timer may be set to 0 to 120 seconds, or approximately 10-20 seconds as examples. If the onset criteria are not met again before expiration of the onset termination timer at block 518, control circuit 206 returns to the non-tachyarrhythmia state at block 502. In some examples, buffers in memory 210 storing detected AT/AF intervals, other PPI data, cardiac electrical signal amplitudes, or other data used for detecting AT/AF or termination of AT/AF may be cleared or partially cleared upon returning to the non-tachyarrhythmia state 402. The AT/AF duration timer and the AT/AF detection timer, both of which may be started upon initially entering the AT/AF onset state, may be reset to zero upon transitioning back to the non-tachyarrhythmia state at block 502. An AT/AF episode is not detected by control circuit 206 when control circuit 206 transitions back to non-tachyarrhythmia state 402 via the pending onset termination state 420.

When control circuit 206 determines that the onset criteria are met at block 516 ("yes" branch) before the onset termination timer expires at block 518 (while operating in the pending onset termination state), control circuit 206 returns to the AT/AF onset state (transition arrow 422 in FIG. 7) at block 506. In this way, AT/AF that is briefly intermittent and/or intermittent undersensing of P-waves during AT/AF (causing termination criteria to be met temporarily) does not cause repeated redetection of an AT/AF episode as separate shorter AT/AF episodes. Once in the AT/AF onset operating state at block 506, control circuit 206 may detect an AT/AF episode in response to the detection timer expiring at block 520 without the termination criteria being met ("no" branch of block 510). For example, control circuit 206 may start the AT/AF detection timer upon initially transitioning to the AT/AF onset state from the non-tachyarrhythmia state. The AT/AF detection timer may be set to a detection time interval of 1, 2, 3, 4, 5, 6, 8, or 10, 20, 30 or 60 minutes as examples, or another selected time interval. In one example, the AT/AF detection timer is set to six minutes. When the termination criteria are not met during the selected AT/AF detection time interval after onset criteria are met (which may include any time spent in the pending onset termination state 420), control circuit 206 detects the AT/AF episode at block 522.

Referring to FIG. 7, the detection timer 416 may not be reset when control circuit 206 transitions to the pending onset termination state 420 in response to termination criteria being met so that it continues to run without interruption if the onset criteria are met again, e.g., within 10 seconds, and control circuit 206 transitions back to the AT/AF onset state 410. When the detection timer 416 expires before the termination criteria are met, control circuit 206 transitions (arrow 414) to AT/AF detection state 430. AT/AF is detected by control circuit 206 upon the transition to the AT/AF detection state 430. Control circuit 206 may generate an output in response to the AT/AF detection, according to any of the examples given herein. For example, data relating to the detected episode may be stored in memory 210 and other detection responses may be performed. For example, in response to transitioning to the AT/AF detection state 430, telemetry circuit 208 may transmit an AT/AF detection notification signal in response to the AT/AF detection flag stored in memory and a control signal from control circuit 206. Control circuit 206 may adjust a therapy delivered by pulse generator 202. Control circuit 206 may disable accelerometer 212 or at least disable rate response pacing based on the accelerometer signal.

Upon transitioning to the AT/AF detection state at block 522 of FIG. 8, any buffers in memory 210 storing PPIs, a count of AT/AF detection intervals, cardiac electrical signal amplitudes or other data relating to the termination criteria may remain stored in memory 210 for use by control circuit 206 for determining when termination criteria are met at block 524. The AT/AF duration timer, when started at block 508 upon initially entering the AT/AF onset state, continues to run for timing the duration of the detected AT/AF episode. In other examples, the AT/AF duration timer may be started at block 522 upon entering the AT/AF detection state. The AT/AF detection timer value may be added to the AT/AF duration timer. During the AT/AF detection state, control circuit 206 continues to analyze PPIs, cardiac electrical signal amplitudes, and/or frequency of delivered atrial pacing pulses for determining when the termination criteria are met at block 524, e.g., using the techniques described below in conjunction with FIG. 11.

In response to the termination criteria being met during the AT/AF detection state at block 524, control circuit 206 transitions (arrow 432 of FIG. 7) to the pending termination state at block 526. Control circuit 206 may start a termination timer (shown as timer 446 in FIG. 7) at block 528. The termination timer may be set to a termination time interval of 0 to 120 seconds or about 20 to 30 seconds, as examples. The AT/AF duration timer continues to run upon transitioning to the pending termination state since termination of the AT/AF episode has not yet been detected. In the pending termination state, control circuit 206 analyzes the cardiac electrical signal at block 530 to determine if the onset criteria are met again before the termination timer expires. If the onset criteria are met before the termination timer expires (block 532), 20 seconds for example, control circuit 206 returns to the AT/AF detection state at block 522 ("yes" branch of block 530). The previously started AT/AF duration timer may continue running without disruption during the transition 432 of FIG. 7 (from the AT/AF detection state to the pending termination state) and the transition 442 (back to the AT/AF detection state from the pending termination state) so that the duration of the detected AT/AF episode is determined without regard to intermittent PPIs greater (longer) than the AT/AF detection interval, e.g., due to under-sensed P-waves, or other cardiac electrical signal changes that may cause the termination criteria to be met briefly at block 524 followed by onset criteria being met again at block 530 within the termination time interval.

In response to the termination timer expiring at block 532 before the onset criteria are met ("no" branch of block 530) in the pending termination state, control circuit 206 detects AT/AF episode termination at block 534 and returns to the non-tachyarrhythmia state at block 502. The detected AT/AF episode is determined to be terminated by control circuit 206 in response to the termination criteria being met (in the AT/AF detection state) and the onset criteria not being met within a termination time interval (in the pending termination state) after the termination criteria are met. The AT/AF duration timer may be cleared after storing the total AT/AF episode duration in memory 210, e.g., along with a date and time stamp, at block 536. Other AT/AF episode data may be stored at block 536, such as the mean or median atrial rate, minimum atrial rate, maximum atrial rate or other episode related data. The total AT/AF episode duration may be determined at block 536 by control circuit 206 as the value of the AT/AF duration timer at the time the termination criteria were met. In some examples, the AT/AF duration timer continues to run during the pending termination state in case onset criteria are met again and control circuit 206 returns to the AT/AF detection state. As such, control circuit 206 may determine and store the AT/AF episode duration at block 536 as the value of the AT/AF duration timer upon transitioning to the non-tachyarrhythmia state (arrow 444 of FIG. 7) less the termination time interval that corresponds to the time spent in the pending termination state 440 after termination criteria were met.

Buffers used for storing cardiac electrical signal data in memory 210, e.g., PPIs, AT/AF interval counts, and/or cardiac electrical signal amplitudes used for determining when termination and onset criteria are met, may be at least partially cleared upon transitioning to the non-tachyarrhythmia state. In other examples, stored data used in determining when onset criteria are met may remain in buffers in memory 210 for use during the non-tachyarrhythmia state at block 502.

In some examples, control circuit 206 buffers a segment of the atrial EGM signal in memory 210 in response to the AT/AF detection during the AT/AF detection state. A 6 to 10 second atrial EGM signal segment may be buffered in memory 210 for example. The segment may be stored in memory 210 for later transmission by telemetry circuit 208 to external device 20, for instance.

In some examples, memory 210 may have limited capacity for storing atrial EGM segments. In this case, control circuit 206 may determine at block 536 if an atrial EGM segment (and/or accelerometer signal) buffered in memory 210 in response to an AT/AF detection overwrites a previously stored EGM segment (and/or acceleration signal segment). In some examples, a more recent atrial EGM segment (and corresponding accelerometer signal segment) overwrites an older segment such that EGM segments (and corresponding acceleration signal segments) are stored on a first-in-first out basis. In other examples, an EGM segment may overwrite an older EGM segment stored in memory 210 based on priority selection criteria, such as the longest AT/AF episode duration, the greatest atrial maximum or median rate, or other selection criteria. In this way, an EGM signal segment (and acceleration signal segment) may be stored in memory 210 at block 536 when the AT/AF duration is longer than any previous stored episodes, when the atrial rate is faster than any previous stored episodes and/or based on other AT/AF episode characteristics that may be indicative of the relative severity or clinical importance of the detected AT/AF episode.

In some examples, control circuit 206 determines the atrial rate during the AT/AF onset state (block 506) and/or during the AT/AF detection state (block 522). For example, the number of atrial events or PPIs may be counted by control circuit 206 beginning from the time that control circuit 206 enters the AT/AF onset state until the detection timer expires. The count of atrial events or PPIs may be determined as an atrial rate metric of the subsequently detected AT/AF episode. Control circuit 206 may compare the atrial rate metric to the atrial rate metric(s) associated with previously stored EGM signal segments. When the atrial rate metric for the currently detected AT/AF episode is faster than the atrial rate metric for a stored AT/AF episode EGM segment, the buffered atrial EGM signal (and/or acceleration signal) associated with the current AT/AF episode may overwrite a previously stored atrial EGM signal segment (and/or acceleration signal) associated with the slower atrial rate metric.

Additionally or alternatively, control circuit 206 may compare the AT/AF episode duration to a previously determined AT/AF episode duration associated with a previously stored EGM segment (and/or acceleration signal). For example, upon transitioning from the pending termination state to the non-tachyarrhythmia state, the current AT/AF episode duration may be determined based on the duration timer value (less the time spent in the pending termination state) and compared to the episode duration(s) associated with stored EGM signal segments. When the duration of the currently detected AT/AF episode is longer than the duration associated with a previously stored EGM segment, the buffered EGM signal segment (and/or acceleration signal segment) may overwrite the previously stored EGM segment (and/or acceleration signal segment). In this way, an EGM signal segment and/or an acceleration signal segment, e.g., a 6 second segment, may be stored for the fastest AT/AF episode and/or the longest AT/AF episode detected. In some instances, the fastest AT/AF episode may not have the longest duration, in which case EGM signal and accelerometer signal segments may be stored for both the fastest and the longest AT/AF episodes at block 536.

Figure 9:
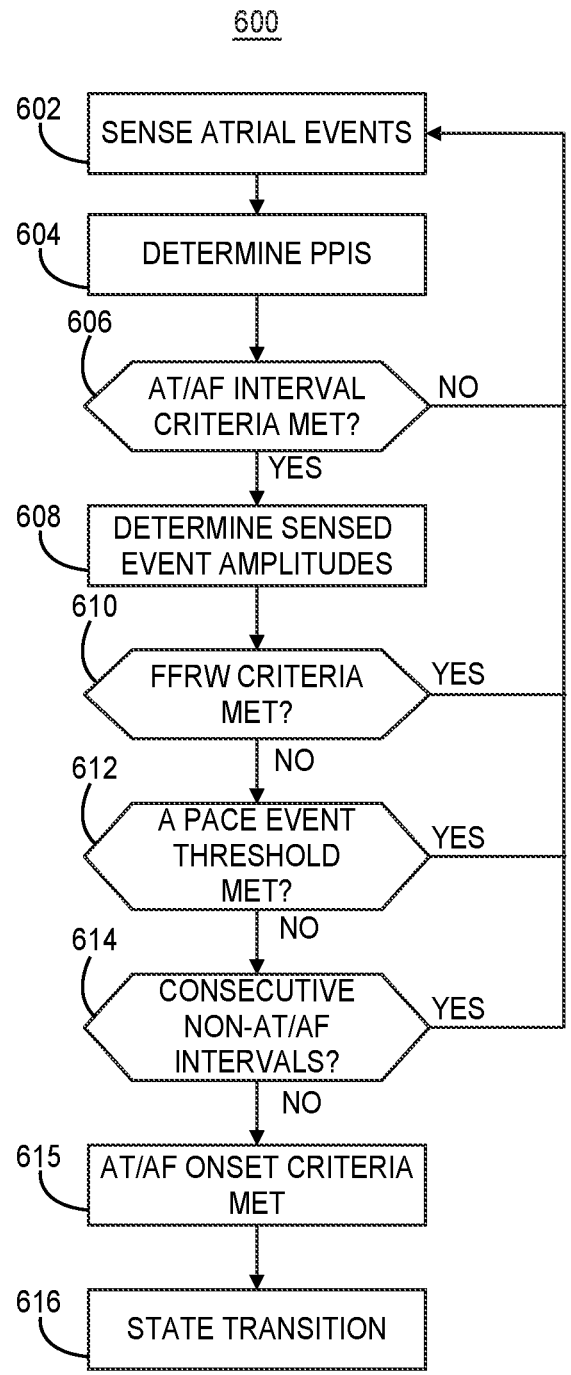
FIG. 9 is a flow chart of a method that may be performed by the atrial pacemaker control circuit for determining when AT/AF onset criteria are met by a sensed cardiac electrical signal according to one example.

FIG. 9 is a flow chart 600 of a method that may be performed by control circuit 206 for determining when onset criteria are met. The method of flow chart 600 may be performed by control circuit 206 while operating in the non-tachyarrhythmia state 402, the pending onset termination state 420 and the pending termination state 440 shown in FIG. 7. Control circuit 206 receives sensed atrial event signals from cardiac electrical signal sensing circuit 204 at block 602 and determines PPIs at block 604. Each PPI is compared to the AT/AF detection interval to identify AT/AF intervals as PPIs that are less (shorter) than the AT/AF detection interval, e.g., less than 300 ms. The PPIs may include intervals determined between an atrial pacing pulse generated by pulse generator 202 to a sensed atrial event signal as well as PPIs between two consecutive sensed atrial event signals. The sensed atrial event signals used in determining PPIs may include both refractory and non-refractory sensed atrial event signals. Control circuit 206 may determine a count of AT/AF intervals out the most recent running number of consecutive PPIs. When a threshold number of AT/AF intervals is reached, e.g., 1 to 24 AT/AF intervals out of 8 to 24 most recent PPIs, control circuit 206 may determine that the AT/AF interval criteria are met at block 606. In other examples, the AT/AF interval criteria may be met when 12 to 20 AT/AF intervals are counted out of the most recent 16 to 24 PPIs.

In response to determining that the AT/AF interval criteria are met at block 606, control circuit 206 may determine if FFRW oversensing criteria are met at block 610. In order to determine when FFRW oversensing criteria are met, control circuit 206 may determine atrial sensed event peak amplitudes at block 608. The maximum peak amplitude of the atrial electrical signal may be determined following each atrial sensed event signal by sensing circuit 204 and passed to control circuit 206 at block 608 and buffered in memory 210. Methods for determining when FFRW oversensing criteria are met are described below in conjunction with FIG. 10. Control circuit 206 may determine, for example, when alternating high and low sensed event amplitudes and/or alternating long and short PPIs are determined as evidence of one or more oversensed FFRWs. Control circuit 206 may classify a sequence of atrial cycles as an FFRW sequence. When a threshold number of FFRW sequences is reached, the FFRW oversensing criteria may be met at block 610.

In examples described below, e.g., in conjunction with FIG. 10, the FFRW sequences may be determined based on sensed atrial event signals and peak amplitude signals received by control circuit 206 from P-wave sensing channel 320 (FIG. 5). FFRW sensing channel 330 may be optional and is not required for determining FFRW sequences in some examples. When FFRW sensing channel 330 is included, the number of sensed FFRW signals and/or the peak amplitude signal from FFRW sensing channel 330 may be used by control circuit 206 in classifying a sequence of atrial cycles as an FFRW sequence, which may be counted toward meeting FFRW oversensing criteria at block 610.

When the FFRW criteria are met ("yes" branch of block 610), control circuit 206 returns to block 602 and continues receiving sensed atrial event signals and determining PPIs. The AT/AF onset criteria are not met when FFRW oversensing criteria are met. When the FFRW criteria are not met ("no" branch of block 610), control circuit 206 determines at block 612 whether a threshold number of recent atrial events are atrial paced events and/or whether a threshold number of most recent, consecutive PPIs are long, non-AT/AF intervals at block 614, e.g., greater (longer) than a non-AT/AF interval threshold.

The non-AT/AF interval threshold may be set equal to the AT/AF detection interval, to a multiple thereof, or the AT/AF detection interval plus a predetermined offset, e.g., plus 50 to 200 ms. In one example, the consecutive non-AT/AF intervals are detected by control circuit 206 at block 614 when at least the most recent two consecutive PPIs are at least 1.25 to 1.5 times the AT/AF detection interval. In some examples, control circuit 206 counts an atrial event interval ending with an atrial pacing pulse generated by the pulse generator as a PPI that is longer than the non-AT/AF detection interval threshold.

When a predetermined number of the most recent atrial events are atrial pacing pulses ("yes" branch of block 612) or atrial sensed event signals are occurring at relatively long, non-AT/AF intervals ("yes" branch of block 614), AT/AF may not be present. For example, when at least one of the most recent three atrial events is an atrial pacing pulse delivered by pulse generator 202 (as determined at block 612) or the most recent two consecutive PPIs are greater than or equal to at least 1.25 times the AT/AF detection interval (as determined at block 614), control circuit 206 may determine that AT/AF onset criteria are not met and return to block 602.

When the AT/AF interval criteria are met (block 606), the FFRW oversensing criteria are not met at block 610, and the atrial pace event criteria at block 612 and the long, non-AT/AF interval criteria at block 614 are not met, control circuit 206 may determine that the onset criteria are met at block 615. In response to determining that the onset criteria are met, control circuit 206 transitions to a different operating state at block 616. In some instances, control circuit 206 transitions from the non-tachyarrhythmia state 402 to the AT/AF onset state 410. In other instances, control circuit 206 is performing the method of flow chart 600 during the pending onset termination state 420 or the pending termination state 440. When the onset criteria are met before an onset termination time interval expires (onset termination timer 426) in the pending onset termination state 420, control circuit 206 returns to the AT/AF onset state 410. When the onset criteria are met at block 614 before a termination time interval expires (termination timer 446) in the pending termination state 440, control circuit 206 returns to the AT/AF detection state 430.

As described above, the process of flow chart 600 may be performed until the onset termination timer expires (when operating in the pending onset termination state) or the termination timer expires (when operating in the pending termination state). If the onset termination timer or the termination timer expires before the AT/AF onset criteria are met (e.g., affirmative result at block 606 and negative results at blocks 610, 612 and 614), the process of flow chart 600 may be terminated. Control circuit 206 may transition to the non-tachyarrhythmia state 402 in response to the onset termination timer or the pending termination timer expiring during the process of flow chart 600.

Figure 10:
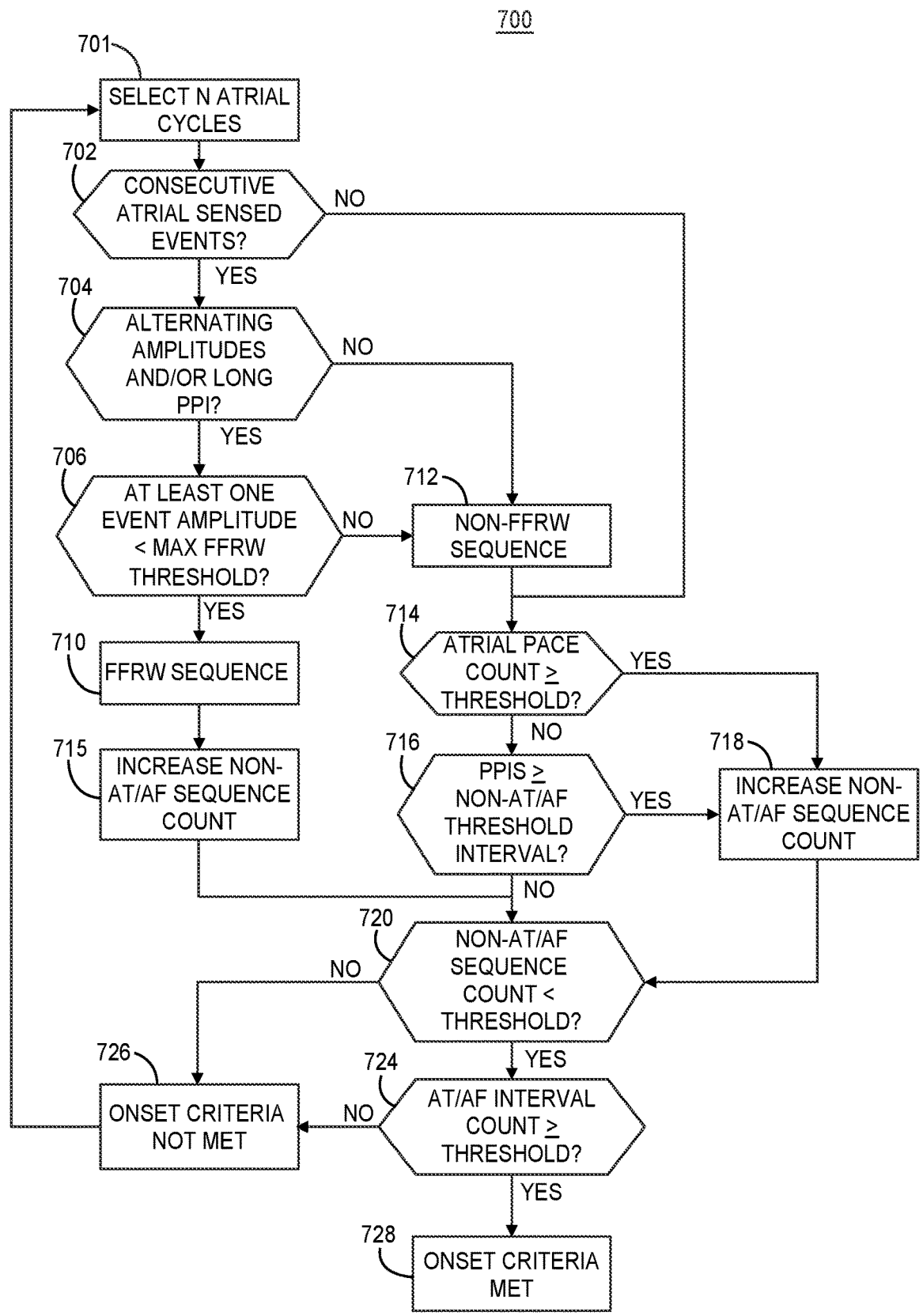
FIG. 10 is a flow chart of a method for classifying atrial cycles as FFRW sequences or non-FFRW sequences for determining when onset criteria are met according to one example.

FIG. 10 is a flow chart 700 of a method for classifying atrial cycles as FFRW sequences or non-FFRW sequences for determining when onset criteria are met according to another example. The process of flow chart 700 may be performed for determining if the onset criteria are met during the non-tachyarrhythmia state 402, the pending onset termination state 420 or the pending termination state 440 as described above in conjunction with FIGS. 7 and 8. At block 701, control circuit 206 may select a sequence of most recent consecutive atrial cycles, which may include both atrial sensed event signals and atrial pacing pulses. The sequence of atrial cycles may be the most recent two atrial cycles defined by the most recent three atrial events, sensed or paced, though a higher number of the most recent atrial cycles may be selected in other examples. For the sake of illustration, the process of flow chart 700 is described below as evaluating the most recent sequence of two atrial cycles including the most recent three atrial events.

At block 702, control circuit 206 may determine whether the sequence of two atrial cycles include all atrial sensed events, e.g., based on three consecutive atrial sensed event signals received from sensing circuit 204. If so, control circuit 206 advances to blocks 704 and 706 to analyze the sequence for classifying the sequence as a non-FFRW sequence or a FFRW sequence. If the sequence of two atrial cycles includes an atrial pacing pulse, as determined at block 702 ("no" branch), control circuit 206 may advance to block 714 to determine if the atrial cycles meet other criteria for classifying the atrial cycle sequence as a non-AT/AF sequence or an AT/AF sequence counted toward meeting the onset criteria.

At blocks 704 and 706, control circuit 206 may apply criteria to the sensed event signals and/or maximum peak amplitude signals from the P-wave sensing channel and/or FFRW sensing channel of sensing circuit 204 for classifying the sequence as an FFRW sequence or a non-FFRW sequence. For example, control circuit 206 determines whether the sequence of atrial cycles that include consecutive atrial sensed events include at least one relatively long PPI and/or have alternating high and low peak amplitudes, e.g., high-low-high or low-high-low. When the most recent sequence of two atrial cycles includes three consecutive atrial sensed events, control circuit 206 may determine if the peak amplitudes of the first and last of the three sensed events are within a similarity threshold of each other and at least a difference threshold (more than or less than) the peak amplitude of the second (middle) one of the three atrial sensed events. Alternatively, control circuit 206 may determine two consecutive peak amplitude differences and detect alternating peak amplitudes in response to the first difference being opposite in sign than the second difference (one negative difference and one positive difference) and the absolute value of each difference being greater than a threshold difference. In another example, control circuit 206 may detect alternating amplitudes when the first peak amplitude and third peak amplitude are both greater than the second peak amplitude or both less than the second peak amplitude.

The sensed events of the sequence of two atrial cycles may be identified by control circuit 206 based on three consecutive atrial sensed event signals received from sensing circuit 204, which may include refractory (sensed during a post-atrial or post-pace refractory period) and/or non-refractory (sensed after the refractory period) sensed event signals. Control circuit 206 may determine the peak amplitudes for the comparisons at block 704 from the EGM signal received from sensing circuit 204 or from the peak amplitude signals received from sensing circuit 204. As described above, P-wave sensing channel 320 of sensing circuit 204 may pass a peak amplitude signal to control circuit 206 indicating the maximum peak of the atrial cardiac electrical signal following a P-wave sensing threshold crossing. When the three consecutive peak amplitude signals received from sensing circuit 204 are alternating in amplitude, control circuit 206 advances to block 706.

Additionally or alternatively, at block 704 control circuit 206 may compare the two PPIs defined by the three consecutive sensed atrial event signals to determine if at least one of the two PPIs is greater than or equal to a long PPI threshold. The long PPI threshold may be set based on the AT/AF detection interval, e.g., a predetermined multiple of the AT/AF detection interval. The long PPI threshold may be set between one and 1.5 times the AT/AF detection interval, e.g., at least 1.25 times the AT/AF detection interval. In response to at least one PPI of two most recent atrial cycles that include three consecutive atrial sensed event signals being equal to or greater than the long PPI threshold, control circuit 206 may advance to block 706.

Control circuit 206 may use the sensed atrial event signals and peak amplitude signals from P-wave sensing channel 320 for determining that the criteria at block 704 are met. In examples that include FFRW sensing channel 330, control circuit 206 may determine if at least one sensed FFRW signal is received during the N atrial cycles in addition to or alternatively to the criteria of alternating peak amplitudes and/or at least one long PPI at block 704.

When control circuit 206 determines that the event amplitudes are not alternating and/or none of the associated PPIs is a long interval (e.g., greater than or equal to the long PPI threshold interval), control circuit 206 determines that the selected N cycles are unlikely to include an oversensed FFRW. Control circuit 206 classifies the atrial cycles as a non-FFRW sequence at block 712.

When control circuit 206 determines that the sensed event peak amplitudes are alternating and/or at least one of the associated PPIs is greater than or equal to the long PPI threshold, control circuit 206 advances to block 706 to determine if at least one of the determined peak amplitudes is less than a maximum FFRW peak amplitude limit. Control circuit 206 may compare the peak amplitude signals received from P-wave sensing channel 320 (FIG. 5) to the maximum FFRW peak amplitude limit. In other examples, when the FFRW sensing channel 330 is included in sensing circuit 204, control circuit 206 may compare the peak amplitude signals received from FFRW sensing channel 330 to the maximum FFRW peak amplitude limit at block 706. If all of the peak amplitudes determined in the N most recent atrial cycles are greater than the maximum FFRW peak amplitude limit ("no" branch of block 706), the sensed atrial events are unlikely to include an oversensed FFRW. Control circuit 206 may classify the most recent N cycles as a non-FFRW sequence at block 712. However, if at least one of the peak amplitudes (from the P-wave sensing channel or the FFRW sensing channel) is less than the maximum FFRW peak amplitude limit at block 706, control circuit 206 may classify the N cycles as an FFRW sequence at block 710. Control circuit 206 may determine that FFRW oversensing criteria are met based on at least the N cycles because the N cycles are determined to likely include at least one oversensed FFRW based on the criteria applied at blocks 704 and 706 being met. The N cycles meeting the criteria applied at block 704 and 706 may be counted as a non-AT/AF sequence, toward a determination of AT/AF termination.

Control circuit 206 may increase a non-AT/AF sequence count at block 715 in response to classifying the FFRW sequence at block 710. Control circuit 206 may track the number of atrial cycle sequences classified as non-AT/AF sequences during the predetermined number of PPIs that are used to determine when onset criteria are met. For example, when X AT/AF intervals out of Y PPIs are required for onset criteria to be met, control circuit 206 may require that less than M out of Y sequences of two atrial cycles each are classified as FFRW sequences. For example, when at least 12 AT/AF intervals out of the most recent 16 PPIs are required to meet the onset criteria, control circuit 206 may count the number of FFRW sequences determined over the 16 PPIs, where each FFRW sequence may represent a consecutive pair of the 16 PPIs. As each sensed event signal is received from sensing circuit 204 or atrial pacing pulse is delivered by pulse generator 202, control circuit 206 may determine if the most recent two atrial cycles (including three atrial events) is an FFRW sequence or a non-FFRW sequence for updating the non-AT/AF sequence count while simultaneously or concomitantly updating the AT/AF interval count out of the most recent Y PPIs. Thus, in some examples, the N atrial cycles selected at block 701 may be overlapping with the previous N atrial cycles evaluated. In other examples, the N atrial cycles selected at block 701 are non-overlapping cycles with the preceding and the subsequent sequences of N atrial cycles.

After updating the non-AT/AF sequence count at block 715, control circuit 206 may compare the non-AT/AF sequence count to a threshold count at block 720. If the non-AT/AF sequence count is less than the threshold at block 720 and the AT/AF interval count is greater than or equal to a required threshold count at block 724, control circuit 206 determines that the onset criteria are met at block 728. To illustrate, when fewer than 10, 12, 14 or other threshold number of FFRW sequences are counted as non-AT/AF sequences out of the most recent 16 PPIs and at least 12 AT/AF intervals out of the 16 PPIs are counted, control circuit 206 may determine that onset criteria are met at block 728. If either the non-AT/AF sequence count is greater than or equal to the threshold count at block 720 or the AT/AF interval count is less than the threshold at block 724, control circuit 206 may determine that onset criteria are unmet at block 726 and return to block 701 to continue analyzing atrial cycles and PPIs, until the onset criteria are met or a timer associated with the current operating state expires causing a state transition.

In some examples, control circuit 206 may increase the non-AT/AF sequence count at block 718 even though the N atrial cycles are classified as a non-FFRW sequence at block 712. Control circuit 206 may increase the non-AT/AF sequence count at block 718 when the selected N atrial cycles include atrial pacing pulses and/or consecutive non-AT/AF intervals to reduce the likelihood of onset criteria from becoming satisfied when the recent N atrial cycles are unlikely to be AT/AF cycles.

As such, when the N atrial cycles are classified as a non-FFRW sequence at block 712, control circuit 206 may determine if the number of atrial pacing pulses in N atrial cycles is greater than a threshold at block 714. In the illustrative example of analyzing the most recent three atrial events corresponding to the most recent two atrial cycles, if at least one atrial event is an atrial pacing pulse, control circuit 206 increases the non-AT/AF sequence count at block 718 ("yes" branch of block 714).

Additionally or alternatively, control circuit 206 may determine at block 716 if a threshold number of the N atrial cycles are longer than a non-AT/AF threshold interval. In the illustrative example of analyzing the most recent two atrial cycles, when both of the two consecutive PPIs are greater than or equal to the non-AT/AF threshold interval, control circuit 206 may increase the non-AT/AF sequence count at block 718. The non-AT/AF threshold interval may be equal to or greater than the AT/AF detection interval and may or may not be equal to the long PPI threshold applied at block 704 for detecting an FFRW sequence. In some examples, the non-AT/AF threshold interval is between 1 and 1.5 times the AT/AF detection interval, or 1.25 times the AT/AF detection interval in one example, which may be equal to the long PPI threshold applied at block 704.

The presence of atrial pacing and/or relatively long, consecutive PPIs during the N atrial cycles may inhibit the determination of onset criteria being met by increasing the non-AT/AF sequence count at block 718. The presence of recent atrial paced events or relatively long, consecutive PPIs in the N atrial cycles causes control circuit 206 to increase the non-AT/AF sequence count as a way of reducing the likelihood of determining that the onset criteria are met.

At block 720, control circuit 206 compares the non-AT/AF sequence count to a threshold. Control circuit 206 may require that the non-AT/AF sequence count be less than M over the most recent Y PPIs where M may be equal to, less than or greater than the number of X AT/AF intervals required over the Y PPIs for onset criteria to be met. In one example M is greater than X in order to determine that onset criteria are not met at block 726. For example, when 12 out 16 PPIs are required to meet the AT/AF interval criteria, control circuit 206 may require that the non-AT/AF sequence count be at least 14 to determine that onset criteria are not met (or less than 14 in order to determine that onset criteria are met). The non-AT/AF sequences may be overlapping sequences such that one atrial sensed event signal that is an oversensed FFRW may be effectively counted more than once in the non-AT/AF sequence count. In some instances, the non-AT/AF sequence count of 14, for example, may correspond to about 7 oversensed FFRWs, accounting for about half of the PPIs that may be counted as AT/AF intervals. In other examples, consecutive atrial cycles selected at block 701 may be selected as non-overlapping sequences of atrial cycles such that the non-AT/AF sequence count is updated less frequently, rather than on each atrial event. The threshold value of M non-AT/AF sequences applied at block 720 may be set lower accordingly, e.g., to 5, 6 or 7 as examples. When the non-AT/AF sequence count is equal to or greater than a threshold count at block 720 ("no" branch of block 720), control circuit 206 determines that the onset criteria are not met at block 726.

If the non-AT/AF sequence count is less than the threshold count at block 720 ("yes" branch), and the AT/AF interval count is less than a threshold count at block 724 ("no" branch, e.g., less than X AT/AF intervals out of Y PPIs), control circuit 206 determines that the onset criteria are not met at block 726. When the non-AT/AF sequence count is less than the threshold count at block 720 and the AT/AF interval count is greater than or equal to required threshold count at block 724 ("yes" branch of block 724), control circuit 206 determines that the onset criteria are met at block 728.

The threshold number of non-AT/AF sequences required for determining that onset criteria are not met may be programmable between 1 and 24, as examples, and will depend in part on the number of Y PPIs being evaluated for meeting onset criteria. The number of Y PPIs may be programmable between 8 and 24 PPIs, for example, such that the threshold number of non-AT/AF sequences applied at block 720 is a portion of the number of Y PPIs. The threshold number of X AT/AF intervals required to determine that onset criteria are met may be programmable between 1 and 24, depending in part on the number of Y PPIs being evaluated. In other examples, the number of Y PPIs may be a predetermined or programmable number between 3 and 100 or 5 and 40, for example, and the threshold number of non-AT/AF sequences and the threshold number of AT/AF intervals applied at blocks 720 and 724, respectively, may each be programmable as respective percentages of the Y PPIs.

As described above in conjunction with FIG. 7, when the AT/AF onset criteria are met at block 728 during the non-tachyarrhythmia state 402, control circuit 206 transitions to the AT/AF onset state 410 (transition 404) and may start the AT/AF detection timer and the AT/AF duration timer. When control circuit 206 is operating in the pending onset termination state 420, and the onset criteria are met at block 728 before the onset termination timer 426 expires, control circuit 206 transitions back to the AT/AF onset state 410 (transition 422). When the onset criteria are met at block 728 before the termination timer 446 expires while control circuit 206 is operating in the pending termination state 440, control circuit 206 may transition from the pending termination state 440 back to the AT/AF detection state 430 (transition 442).

Figure 11:
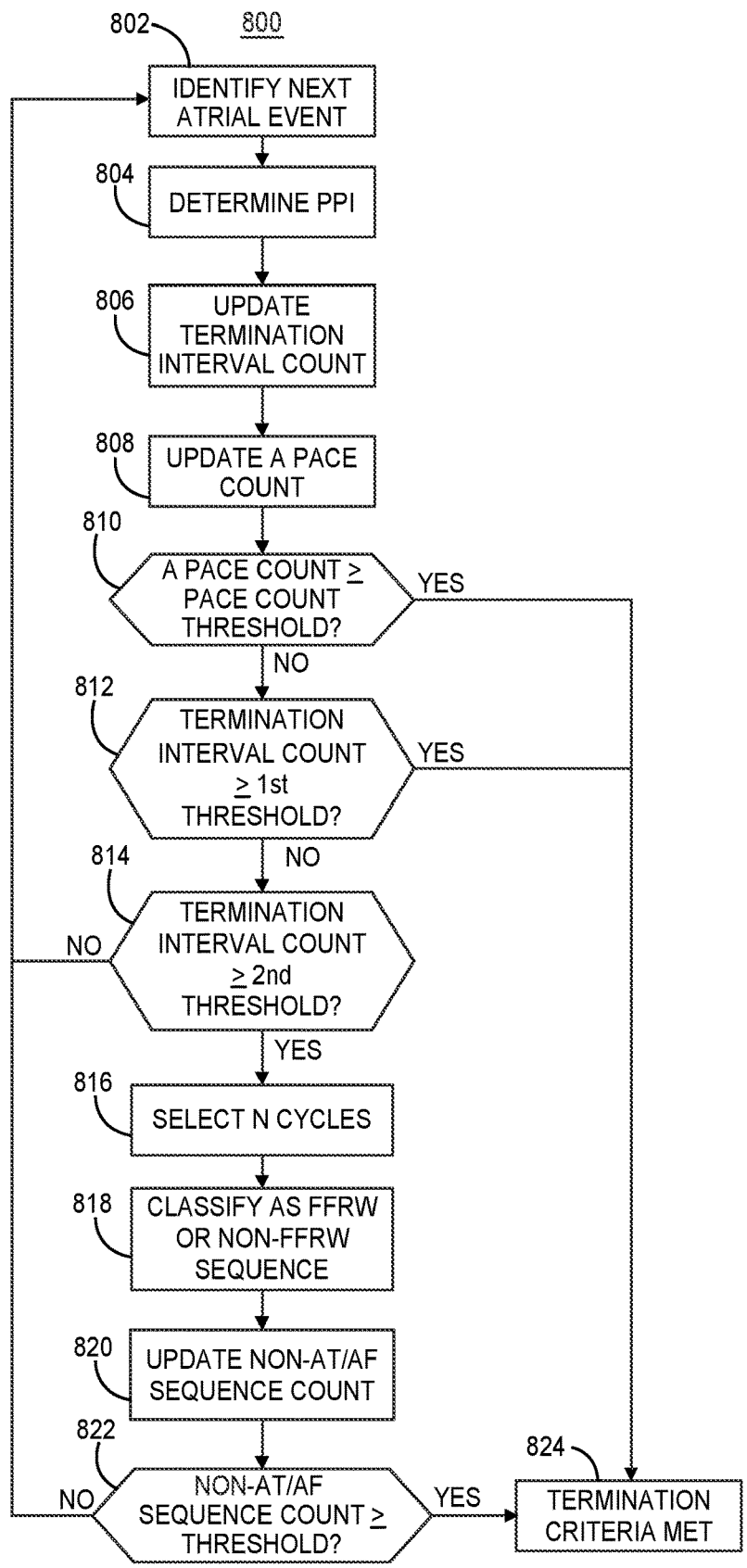
FIG. 11 is a flow chart of a method that may be performed by the atrial pacemaker control circuit for determining that AT/AF termination criteria are met by the cardiac electrical signal according to one example.

FIG. 11 is a flow chart 800 of a method that may be performed by control circuit 206 for determining that termination criteria are met according to some examples. The process of flow chart 800 may be performed when the control circuit 206 is in the pending AT/AF onset state 410 or the AT/AF detection state 430 as shown in FIG. 7. At block 802, control circuit 206 identifies an atrial event, which may be an atrial sensed event signal from cardiac electrical signal sensing circuit 204 or an atrial pacing pulse generated by pulse generator 202. In response to an atrial event, control circuit 206 determines the PPI from the most recent preceding atrial event to the current atrial event at block 804. The PPI may be stored in memory 210, e.g., on a first-in-first-out rolling basis, in a buffer that is storing a predetermined number of PPIs used for determining when termination criteria are satisfied.

At block 806, control circuit 206 updates a termination interval count based on the current PPI determined at block 804. Each PPI may be compared to a termination interval threshold at block 806 to determine an updated termination interval count at block 806. The termination interval threshold may be set equal to or greater than the AT/AF detection interval. In some examples, the termination interval threshold is set to a multiple of the AT/AF detection interval, e.g., 1 to 1.5 times the AT/AF detection interval. At block 806, control circuit 206 may determine that the PPI is a termination interval if it is greater than the termination interval threshold and update the count of termination intervals out of the most recent PPIs buffered in memory 210. In some examples, control circuit 206 counts an atrial event interval ending with an atrial pacing pulse generated by the pulse generator as a termination interval. In some examples, if a refractory atrial sensed event signal is sensed during the atrial pacing interval ending with a delivered pacing pulse, control circuit 206 may ignore the refractory atrial sensed event signal and count the atrial cycle ending with the atrial pacing pulse as a termination interval.

At block 808, control circuit 206 may update an atrial pacing pulse count in response to the current atrial event. Control circuit 206 may track the number of atrial pacing pulses delivered out of a most recent predetermined number of atrial events. For example, control circuit 206 may track the number of atrial pacing pulses delivered out of the most recent five to ten atrial events, which may include atrial sensed event signals and/or atrial pacing pulses. A high percentage of atrial pacing pulses out of the predetermined number of atrial events may be evidence that AT/AF intervals are non-sustained (such that returning to the AT/AF onset state from the pending onset termination state is not warranted) or a detected AT/AF episode is terminated.

As such, at block 810 control circuit 206 may determine if the updated atrial pacing pulse count is equal to or greater than a pace count threshold. In some examples, control circuit 206 may determine that the pace count threshold is reached when at least 80%, 90% or 100% of the most recent three to ten (or other selected number of) atrial events are atrial pacing pulses. In one example, control circuit 206 updates the atrial pacing pulse count to track the number of atrial pacing pulses out of the most recent five atrial events. When the most recent five atrial events are all atrial pacing pulses, the atrial pacing pulse count is determined to be equal to the pace count threshold at block 810.

In some examples, refractory atrial sensed event signals may be ignored by control circuit 206 when identifying the most recent five atrial events and determining the atrial pacing pulse count. For example, if the most recent five atrial events excluding any refractory atrial sensed events are all atrial pacing pulses, the pace count threshold is determined to be reached by control circuit 206 at block 810. The atrial events may include intervening refractory atrial sensed event signals but no non-refractory atrial sensed event signals in some examples. In response to the pace count threshold being reached ("yes" branch of block 810), control circuit 206 determines that termination criteria are met at block 824.

When the pace count threshold is not reached, control circuit 206 may determine whether the updated termination interval count is greater than or equal to a first threshold count at block 812. The first termination threshold count may be set to a relatively high percentage, e.g., 70% or higher, of a predetermined number of most recent PPIs. In one example, at least 18 termination intervals out of 24 PPIs are required to meet the first threshold count at block 812. The predetermined number of PPIs evaluated and buffered in memory 210 may be 8 to 40 PPIs in various examples. The first termination threshold count may be programmable up to 100% of the predetermined number of PPIs. When the first termination threshold count is reached or exceeded, control circuit 206 may determine that the termination criteria are met at block 824 ("yes" branch of block 812).

However, when the first termination threshold is not met at block 812, control circuit 206 may compare the termination interval count to a second, lower termination threshold count at block 814. In order to promote termination detection in the presence of FFRW oversensing, a lower termination threshold count, in combination with other FFRW oversensing criteria, may satisfy the termination criteria. The second lower termination threshold count may require that at least 20% to 60% or about 40% of the most recent PPIs are determined to be termination intervals, as examples. For instance, when at least 10 out of the most recent 24 PPIs are counted as termination intervals, control circuit 206 may determine that the second termination threshold count is reached at block 814. If the termination interval count is less than the second termination threshold count ("no" branch of block 814), control circuit 206 returns to block 802. Termination criteria are not satisfied. Control circuit 206 remains in the AT/AF onset state 410 as long as the AT/AF detection timer 416 has not expired (as shown in FIG. 7) or in the AT/AF detection state 430 until the termination criteria are met.

In some cases, the patient may remain in chronic, persistent AT/AF in which case control circuit 206 may be configured to suspend the termination detection algorithm shown in FIG. 11 when the termination criteria are not met, as determined by control circuit 206, after a predefined time period has expired, e.g., after a several minutes, hours, one day or more. The termination detection algorithm may be re-enabled periodically up to a maximum number of times and/or suspended permanently when the termination criteria remain unsatisfied in the AT/AF detection state for a maximum time limit.

When control circuit 206 determines that the termination interval count reaches or exceeds the second termination threshold count at block 814, control circuit 206 may select the most recent N atrial cycles for classifying the sequence of N cycles as an FFRW sequence or a non-FFRW sequence at block 818 and updating a non-AT/AF sequence count at block 820. As described above in conjunction with FIG. 10, a sequence of N atrial cycles, e.g., two atrial cycles, may be classified as an FFRW sequence when the peak amplitudes associated with the three atrial events of the two atrial cycles are alternating high-low-high or low-high-low and/or at least one PPI is long (e.g., at least 1.25 times the AT/AF detection interval) and/or at least one of the sensed event peak amplitudes is less than a maximum FFRW peak amplitude limit. Any of the example techniques described above for classifying a sequence of atrial cycles as an FFRW sequence or a non-FFRW sequence may be used at block 818.

At block 820, control circuit 206 may update a non-AT/AF sequence count. When the most recent N cycles are classified as an FFRW sequence, the non-AT/AF sequence count is increased at block 820. In some examples, control circuit 206 may increase the non-AT/AF sequence count at block 820 when the sequence is classified as an FFRW sequence or in response to the presence of at least one atrial pacing pulse in the N cycles or all of the N cycles being longer than a non-AT/AF threshold interval. Any of the example techniques described in conjunction with FIG. 10 for updating a non-AT/AF sequence count may be used by control circuit 206 at block 820 for determining when termination criteria are met. A high non-AT/AF sequence count, based on evidence of FFRW oversensing, atrial pacing and/or long PPIs (greater than the termination interval threshold), increases the likelihood of detecting termination of a detected AT/AF episode (or termination of a pending AT/AF detection when operating in the AT/AF onset state 410).

As such, when the non-AT/AF sequence count is greater than or equal to a predetermined threshold at block 822, control circuit 206 determines that termination criteria are met at block 824. In this way, control circuit 206 is configured to detect AT/AF termination in the presence of FFRW oversensing sequences and/or atrial pacing in combination with some relatively long PPIs, but not enough long PPIs to reach the first, higher termination interval threshold count at block 812. If the non-AT/AF sequence count is less than the threshold at block 822, control circuit 206 returns to block 802 without determining that termination criteria are met.

In some examples, at least 70%, 80%, 85% or 90% of the PPIs being evaluated may be required to be classified as being included in non-AT/AF sequences in order for the termination criteria to be met. For instance, when 24 PPIs are being evaluated, the non-AT/AF sequence count may be required to be at least 20 to 22 out of 24 two-cycle sequences evaluated, which may be overlapping two-cycle sequences. In this way, when at least 30% to 40% (second lower threshold applied at block 814) but less than 70% to 80% (first higher threshold applied at block 812) of the PPIs are long, if at least 70% to 90% of the N cycle sequences are non-AT/AF sequences, termination criteria may still be determined to be met by control circuit 206. In an illustrative example, when at least 10 out of 24 PPIs are counted as termination intervals and at least 22 out of 24 N cycle sequences are non-AT/AF sequences, control circuit 206 determines that termination criteria are met (even though the termination interval count may be less than the first threshold applied at block 812).

In response to termination criteria being met at block 824, control circuit 206 may transition to a different state as shown in FIG. 7. For example, if the termination criteria are met during the AT/AF onset state 410 before the AT/AF detection timer 416 expires, control circuit 206 transitions to the pending onset termination state 420 (transition 412). If the termination criteria are met while control circuit 206 is operating in the AT/AF detection state 430, control circuit 206 transitions to the pending termination state 440 (transition 432).

It is to be understood that while blocks 804-822 are shown in a particular order in FIG. 11, the determination by control circuit 206 as to whether termination criteria are met based on an atrial pace count, a termination interval count and/or a non-AT/AF sequence count (which includes counts of FFRW sequences, paced sequences and/or long, non-AT/AF interval sequences) may be performed in a different order than shown or in parallel processes in various examples. Furthermore, in the flow charts and examples presented herein, processing and analysis of the atrial electrical signal and various decision steps for determining when AT/AF onset criteria and AT/AF termination criteria are satisfied may be performed in a different order and/or combination than the order and combinations shown in the illustrative examples and/or in parallel processing operations.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
   a sensing circuit configured to:
      sense a cardiac electrical signal; and
      sense atrial P-waves from the cardiac electrical signal;
   a control circuit configured to:
      detect an atrial tachyarrhythmia based on the sensed cardiac electrical signal;

determine that far field oversensing criteria are met by the cardiac electrical signal due to oversensing of far field R-waves as atrial P-waves by the sensing circuit during the detected atrial tachyarrhythmia;
detect termination of the atrial tachyarrhythmia in response to at least the far field oversensing criteria being met; and
generate an output in response to detecting the termination of the atrial tachyarrhythmia;
a memory configured to store the output generated by the control circuit; and
a pulse generator configured to deliver a therapy and being controlled by the control circuit to adjust the therapy according to the output; and
a telemetry circuit configured to transmit an atrial tachyarrhythmia detection notification in response to the control circuit detecting the atrial tachyarrhythmia.

2. The medical device of claim 1, wherein the control circuit is further configured to detect the termination of the atrial tachyarrhythmia by:
starting a termination time interval in response to determining that the far field oversensing criteria are met;
during the termination time interval, determining whether atrial tachyarrhythmia onset criteria are met based on at least the cardiac electrical signal; and
detecting the termination of the atrial tachyarrhythmia in response to the termination time interval expiring and the atrial tachyarrhythmia onset criteria not being met.

3. The medical device of claim 1, wherein the control circuit is further configured to determine that the far field oversensing criteria are met by:
identifying a plurality of sequences of atrial cycles, each of the plurality of sequences comprising at least two consecutive atrial cycles;
classifying each of the plurality of sequences of atrial cycles as one of a far-field R-wave sequence or a non-far field R-wave sequence;
determining that a threshold number of the plurality of sequences are classified as far-field R-wave sequences; and
determining that the far field oversensing criteria are met when at least the threshold number of the plurality of sequences are classified as far-field R-wave sequences.

4. The medical device of claim 3, wherein:
the sensing circuit is further configured to:
set a P-wave sensing threshold; and
generate an atrial sensed event signal in response to the cardiac electrical signal crossing the P-wave sensing threshold; and
the control circuit is further configured to classify a sequence of the plurality of sequences as a far field R-wave sequence in response to:
determining that at least one peak amplitude of the cardiac electrical signal corresponding to one of at least three consecutive atrial sensed event signals is less than a far field R-wave peak amplitude limit, and at least one of:
determining a pattern of alternating peak amplitudes of the cardiac electrical signal corresponding to at the least three consecutive atrial sensed event signals, or
determining an atrial event interval between a consecutive pair of the at least three consecutive atrial sensed event signals that is greater than a predetermined long interval threshold.

5. The medical device of claim 1, wherein:
the pulse generator is configured to generate atrial pacing pulses; and
the control circuit is further configured to:
determine that a threshold number of atrial pacing pulses are generated during the detected atrial tachyarrhythmia;
start a termination time interval in response to at least the threshold number of atrial pacing pulses being generated during the detected atrial tachyarrhythmia;
during the termination time interval, determine that atrial tachyarrhythmia onset criteria are not met based on at least the far field oversensing criteria being met; and
detect the termination of the atrial tachyarrhythmia in response to the termination time interval expiring and the atrial tachyarrhythmia onset criteria not being met.

6. The medical device of claim 1, wherein:
the sensing circuit is further configured to:
set a P-wave sensing threshold; and
generate an atrial sensed event signal in response to the cardiac electrical signal crossing the P-wave sensing threshold; and
the control circuit is further configured to:
determine atrial event intervals between consecutive atrial events comprising the atrial sensed event signals generated by the sensing circuit;
during the detected atrial tachyarrhythmia, determine that a threshold number of the atrial event intervals are longer than a predetermined termination interval threshold;
start a termination time interval in response to the threshold number of the atrial event intervals being longer than the predetermined termination interval threshold;
during the termination time interval, determine that atrial tachyarrhythmia onset criteria are not met based on at least the far field oversensing criteria being met; and
detect the termination of the atrial tachyarrhythmia in response to the termination time interval expiring and the atrial tachyarrhythmia onset criteria not being met.

7. The medical device of claim 6, wherein:
the pulse generator is configured to generate atrial pacing pulses; and
the control circuit is configured to count an atrial event interval ending with an atrial pacing pulse generated by the pulse generator in the threshold number of the atrial event intervals that are longer than the predetermined termination interval threshold.

8. The medical device of claim 1, wherein:
the sensing circuit is further configured to:
set a P-wave sensing threshold; and
generate an atrial sensed event signal in response to the cardiac electrical signal crossing the P-wave sensing threshold; and
the control circuit is further configured to:
during the detected atrial tachyarrhythmia, determine a plurality of atrial event intervals comprising atrial sensed event signals generated by the sensing circuit;
determine a count of the plurality of atrial event intervals that are longer than a predetermined termination interval threshold;
start a termination time interval in response to one of:
determining that the count of the plurality of atrial event intervals that are longer than the predetermined termination interval threshold is greater than a first threshold, or determining that the count of the plurality of atrial event intervals that are longer than the predetermined termination interval threshold is less than the first threshold and greater than a second threshold and that the far field oversensing criteria are met;

during the termination time interval, determine that atrial tachyarrhythmia onset criteria are not met based on at least the far field oversensing criteria being met; and detect the termination of the atrial tachyarrhythmia in response to the termination time interval expiring and the atrial tachyarrhythmia onset criteria not being met.

9. The medical device of claim 1, wherein the control circuit is further configured to detect the atrial tachyarrhythmia by:

determining that atrial tachyarrhythmia onset criteria are met by the cardiac electrical signal;

starting a detection time interval;

determining that termination criteria are unmet by the cardiac electrical signal prior to an expiration of the detection time interval; and detecting the atrial tachyarrhythmia in response to the detection time interval expiring with the termination criteria being unmet.

10. The medical device of claim 1, further comprising an accelerometer configured to sense an acceleration signal, wherein the control circuit is further configured to store a segment of the acceleration signal in the memory in response to detecting the atrial tachyarrhythmia.

11. The medical device of claim 1, wherein the control circuit is further configured to detect the atrial tachyarrhythmia by:

determining that atrial tachyarrhythmia onset criteria are met a first time by the cardiac electrical signal;

starting a detection time interval in response to the atrial tachyarrhythmia onset criteria being met the first time;

determining that termination criteria are met by the cardiac electrical signal prior to expiration of the detection time interval;

starting a pending onset termination time interval with the detection time interval still running;

determining that the atrial tachyarrhythmia onset criteria are met a second time by the cardiac electrical signal prior to the pending onset termination time interval expiring; and detecting the atrial tachyarrhythmia in response to expiration of the detection time interval.

12. The medical device of claim 1, wherein:

the sensing circuit comprises:

a P-wave sensing channel configured to:

set a P-wave sensing threshold;

sense atrial events in response to the cardiac electrical signal crossing a P-wave sensing threshold; and a far-field R-wave sensing channel configured to:

set a far-field R-wave sensing threshold;

set a far-field R-wave sensing window; and sense far-field R-waves in response to the cardiac electrical signal crossing the far-field R-wave sensing threshold during the far-field R-wave sensing window; and the control circuit is further configured to determine that the far field oversensing criteria are met based on the atrial events sensed by the P-wave sensing channel and the far-field R-waves sensed by the far-field R-wave sensing channel.

13. The medical device of claim 1 wherein the pulse generator is further configured to generate pacing pulses according to a pacing therapy in response to the control circuit detecting the atrial tachyarrhythmia.

14. The medical device of claim 1 further comprising a housing enclosing the sensing circuit and the control circuit, the housing comprising a pair of housing-based electrodes coupled to the sensing circuit for sensing the cardiac electrical signal.

15. The medical device of claim 14, wherein the pulse generator is further configured to deliver the therapy by generating pacing pulses, wherein the pair of housing-based electrodes includes an electrode configured to deliver pacing pulses generated by the pulse generator to a His-Purkinje conduction system of a heart.

16. The medical device of claim 15, wherein the control circuit is further configured to:

control the pulse generator to generate pacing pulses delivered by the electrode according to a first pacing mode in response to detecting the atrial tachyarrhythmia; and control the pulse generator to generate pacing pulses delivered by the electrode according to a second pacing mode different than the first pacing mode in response to detecting termination of the atrial tachyarrhythmia.

17. A non-transitory, computer-readable storage medium storing a set of instructions which, when executed by a control circuit of a medical device, cause the medical device to:

sense a cardiac electrical signal;

sense atrial P-waves from the cardiac electrical signal;

detect an atrial tachyarrhythmia based on the sensed cardiac electrical signal;

determine that far field oversensing criteria are met by the cardiac electrical signal due to oversensing of far field R-waves as atrial P-waves by the sensing circuit during the detected atrial tachyarrhythmia;

detect termination of the atrial tachyarrhythmia in response to at least the far field oversensing criteria being met;

generate an output in response to detecting the termination of the atrial tachyarrhythmia;

store the output in a memory of the medical device;

adjust a therapy delivered by a pulse generator according to the output; and transmit an atrial tachyarrhythmia detection notification in response to detecting the atrial tachyarrhythmia.

18. The non-transitory, computer-readable storage medium of claim 17, wherein the instructions further cause the medical device to:

detect the termination of the atrial tachyarrhythmia by:

starting a termination time interval in response to determining that the far field oversensing criteria are met;

during the termination time interval, determine if atrial tachyarrhythmia onset criteria are met based on at least the cardiac electrical signal; and detecting the termination of the atrial tachyarrhythmia in response to the termination time interval expiring and the atrial tachyarrhythmia onset criteria not being met.

19. The non-transitory, computer-readable storage medium of claim 17, wherein the instructions further cause the medical device to:

identify a plurality of sequences of atrial cycles, each of the plurality of sequences comprising at least two consecutive atrial cycles;

classify each of the plurality of sequences as one of a far-field R-wave sequence or a non-far field R-wave sequence;
determine that a threshold number of the plurality of sequences are classified as far-field R-wave sequences; and
determine that the far field oversensing criteria are met when at least the threshold number of the plurality of sequences are classified as far-field R-wave sequences.

\* \* \* \* \*